(12) United States Patent  (10) Patent No.: US 6,525,322 B2
Wong et al.  (45) Date of Patent: Feb. 25, 2003

(54) METHOD AND APPARATUS TO PREVENT SIGNAL PILE-UP

(75) Inventors: Wai-Hoi Wong, Houston, TX (US); Hongdi Li, Houston, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 4 days.

(21) Appl. No.: 09/957,122

(22) Filed: Sep. 20, 2001

(65) Prior Publication Data

US 2002/0121603 A1 Sep. 5, 2002

Related U.S. Application Data

(62) Division of application No. 09/074,274, filed on May 7, 1998, now Pat. No. 6,310,349
(60) Provisional application No. 60/045,836, filed on May 7, 1997.

(51) Int. Cl.[7] .............................................. G01T 1/208
(52) U.S. Cl. .................. 250/363.09; 250/369; 327/336; 702/194
(58) Field of Search ........................... 250/363.09, 369, 250/395; 327/336, 339, 346; 702/194, 195

(56) References Cited

U.S. PATENT DOCUMENTS

| | | | |
|---|---|---|---|
| 3,747,001 A | 7/1973 | Fasching et al. | 328/116 |
| 4,455,616 A | 6/1984 | Inbar | 364/527 |
| 4,727,256 A | 2/1988 | Kumazawa | 250/370 |
| 4,999,501 A | 3/1991 | Lacy | 50/385.1 |
| 5,319,204 A | 6/1994 | Wong | 250/363.03 |
| 5,393,982 A | 2/1995 | Mott et al. | 250/370.06 |
| 5,430,406 A | 7/1995 | Kolodziejczyk | 327/336 |
| 5,453,623 A | 9/1995 | Wong et al. | 250/363.03 |
| 5,532,944 A | 7/1996 | Battista | 364/602 |

OTHER PUBLICATIONS

Heath, "Inorganic scintillators: A review of techniques and applications," *Nuclear Instruments and Methods*, 162:431–476, 1979.

Lewellen et al., "Evaluation of a clinical scintillation camera with pulse tail extrapolation electronics," *J. Nucl. Med.*, 30:1554–1558, 1989.

Miyaoka et al., "Coincidence mode imaging using a standard dual–header gamma camera," *J. Nucl. Med.*, (37)5:223, 1996.

Muehllehner et al., "SPECT scanner with PET coincidence capability," *J. Nucl. Med.*, (36)5:70, 1995.

Tanaka et al., "Variable sampling–time technique for improving count rate performance of scintillation detectors," *Nuclear Instruments and Methods*, 158:459–466, 1979.

Wong and Li, "A scintillation detector signal processing technique with active pileup prevention for extending scintillation count rates," *IEEE Trans. Nucl. Sci.*, 45(3):838:842, 1998.

(List continued on next page.)

*Primary Examiner*—Georgia Epps
*Assistant Examiner*—Richard Hanig
(74) *Attorney, Agent, or Firm*—Fulbright & Jaworski

(57) ABSTRACT

Gamma cameras and positron (PET) cameras use scintillation detectors to detect radiation from the body. However, when the number of radiation particles that strike the detector is very high, the chance that signals from two or more individual particles will pile up in the detector (to produce one erroneous, larger signal) is high. This problem is common to all applications using scintillation detectors. The present invention discloses methods and apparatus to prevent and correct for this problem. Results from a circuit according to the present invention show at least a 10 fold improvement in the maximum detection-rate limit over the conventional method.

15 Claims, 14 Drawing Sheets

OTHER PUBLICATIONS

Wong et al., "A 2–D detector decoding study on BGO array with quadrant sharing photomulltipiers," *IEEE Trans. Nucl. Sci.*, 41:1453–1457, 1994.

Wong et al., "A high count rate position decoding and energy measuring method for nuclear cameras using anger logic detectors," *IEEE Trans. Nucl. Sci.*, 45(3):1122–1127, 1998.

Wong et al., "A pileup prevention method for gamma cameras," Univ. of TX MD Anderson Cancer Center/ The Society of Nuclear Medicine 44th Annual Meeting (Abstract), 1997.

International Search Report dated Oct. 23, 1998 (PCT/US98/09347)(UTFC:53IP).

FIG. 12A
FIG. 12B
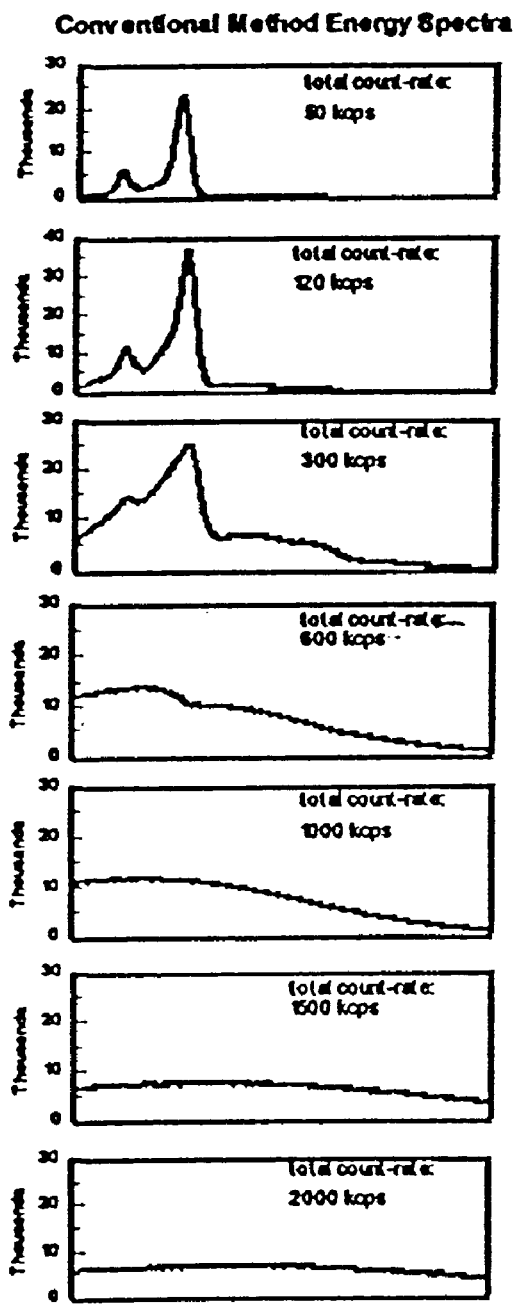
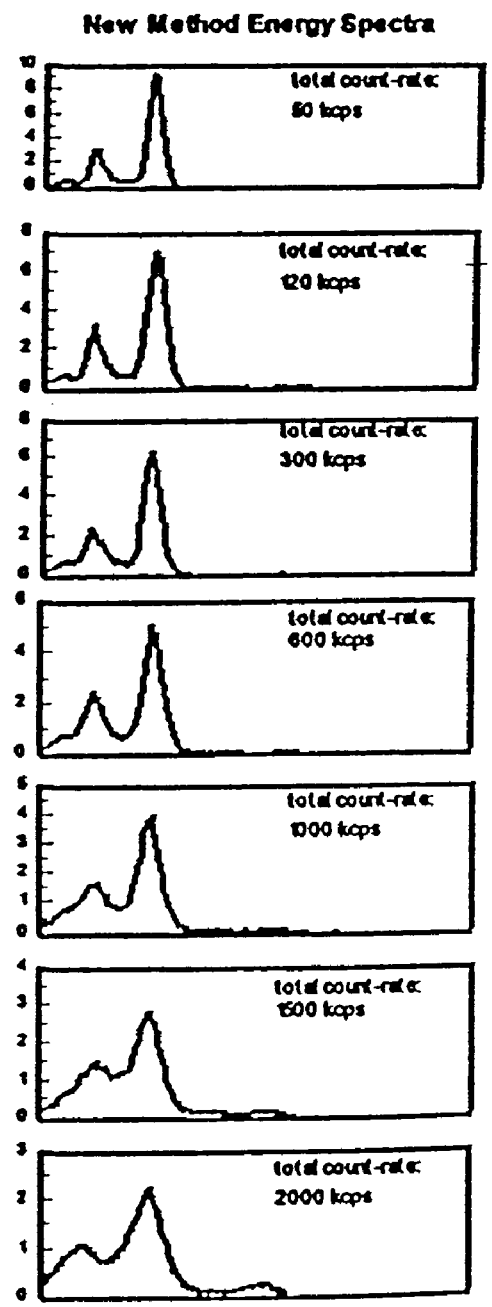
$^{99m}$Tc energy spectra comparison between the standard and new methods for a 3"x4" NaI(Tl) with a 2" PMT. Pulse shaping time for the standard method is 0.5μs.

FIG. 13A 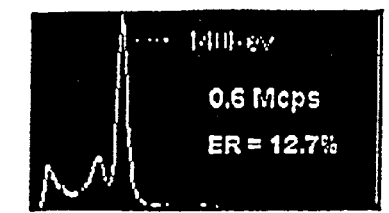 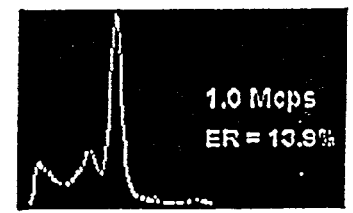 FIG. 13B
FIG. 13C 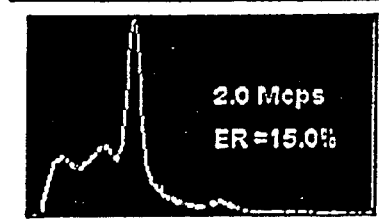 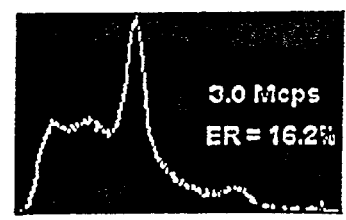 FIG. 13D
FIGS. 13A-D  NaI(Tl) energy spectra of PPE at very high count rates for $^{99m}$Tc. ER = Energy Resolution.
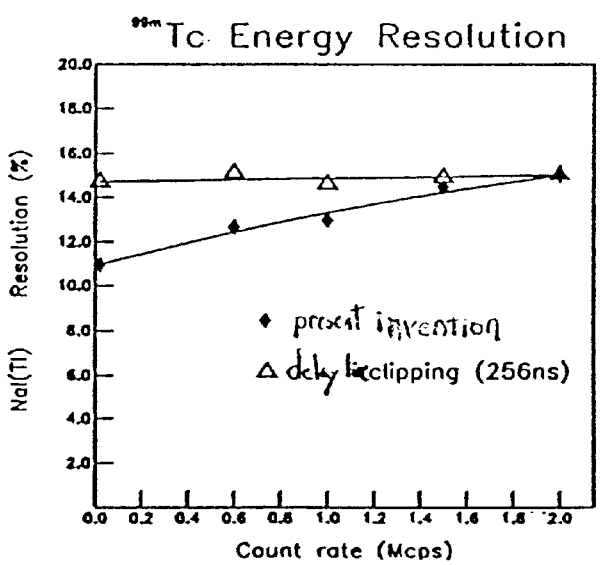
FIG. 14  Energy resolution as a function of count rates

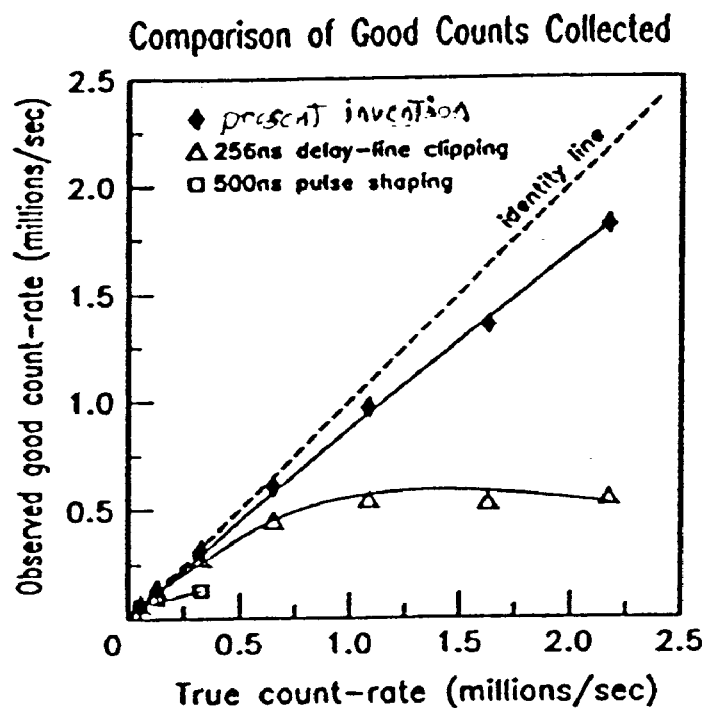
FIG. 15  Photopeak (non-pileup) count rates as a function
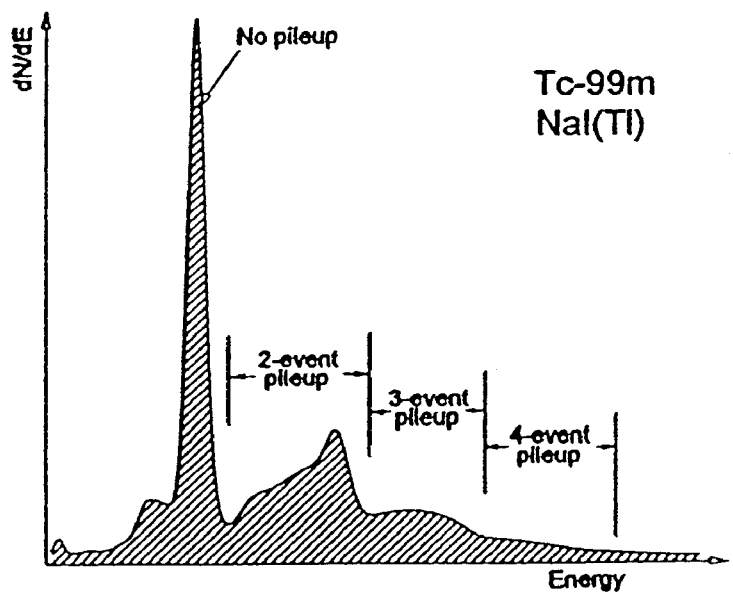
FIG. 16  Delay-line pulse-clipping (256 ns) energy spectrum of
⁹⁹ᵐTc at 2×10⁶ cps. The pileup fraction is larger than the
'area under the curve' indicates because each count in the
pileup region is made up of several counts.

FIG. 17A 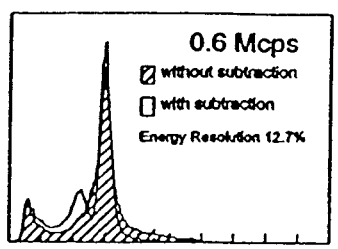 FIG. 17B 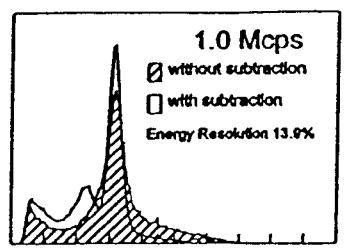
FIG. 17C 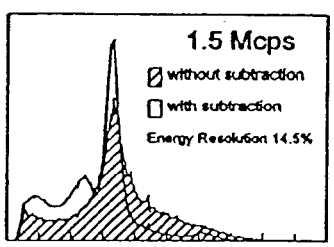 FIG. 17D
FIG. 17E 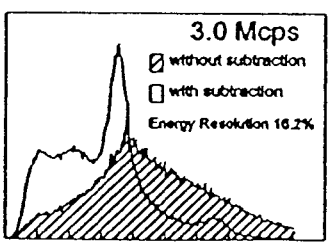 FIG. 17F 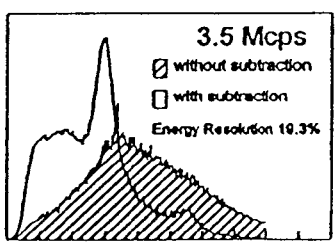
$^{99m}$Tc spectra with and without remnant subtraction

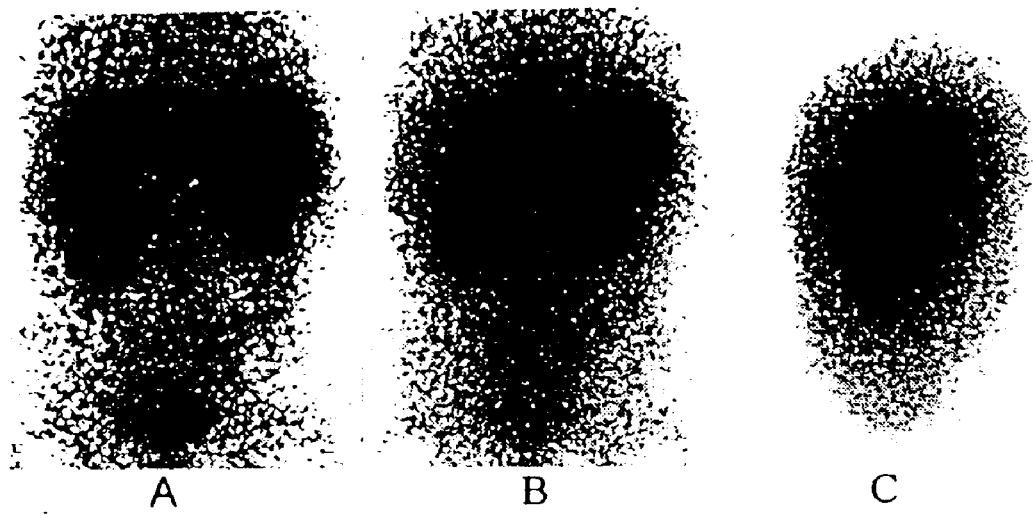
Monte Carlo results: (A) pileup prevention method,
(B) pulse clipping (256 ns clipping), (C) conventional method
(1 μs integration time). Simulated count-rate is $2 \times 10^6$ cps. Within
1 μs, the non-pileup fraction is only 13%, the 2-γ pileup fraction is
27%, and multiple-event (≥3 events) pileup fraction is 60%.
FIG. 18A-C

METHOD AND APPARATUS TO PREVENT SIGNAL PILE-UP

This is a divisional application Ser. No. 09/074,274, filed May 7, 1998 now U.S. Pat. No. 6,310,349.

The government may own rights in the present invention pursuant to grant numbers NIH-RO1-CA61880, NIH-RO1-CA58980, NIH-RO1-CA76246, and NIH-RO1-CA58980S1 from the National Institutes of Health—National Cancer Institute. This invention claims the benefit of U.S. Provisional Application Ser. No. 60/045,836, by Wai-Hoi Wong, et al., filed May 7, 1997.

BACKGROUND OF THE INVENTION

1. Field of the Invention

The present invention relates generally to the field of radiation detection and imaging technology.

2. Description of Related Art

When a radiation particle (gamma ray, neutron, electron, etc.) is detected in a scintillation detector, the scintillation detector will emit light, which is then converted into an electronic signal by a photosensor (e.g., photomultiplier tube or photodiode). This electronic signal can then be received and processed by electronic circuits. In the period after radiation hits the scintillation detector, the scintillation light decays exponentially with a time constant $\tau$ (the time when the light level decays to 37% of the onset level), as shown in FIG. 1.

FIG. 1 shows energy output by two gamma ray particles over time. Since the total amount of light emitted by the scintillation detector represents linearly the energy deposited by the radiation particle in the detector, the area or integral under the curves in FIG. 1 is a measure of the particle energy. As shown in FIG. 1, area 5 and area 10 define a measure of the particle energy of the gamma ray particles. Furthermore the initial peak in the light level is also proportional to the radiation energy. Hence both the area 5 and peak V1 in FIG. 1 may be used to measure the energy of the gamma ray or radiation particle. Since the area under the curve (integral of light) includes many more light signals than the instantaneous peak light level, the integral (the total amount of light emitted) is generally used to measure the radiation energy.

As the radiation flux increases, it becomes increasingly likely that the next radiation particle may arrive at the detector while all previous events are still emitting light (FIG. 2). In this case, the identity of each individual radiation particle will be lost, and several particles will merge into one large signal, as shown in FIG. 2. In this case neither the peak level (V1 or V2 of FIG. 1), nor the integral information (area 5 or area 10 of FIG. 1) can be used to separate or measure the energy of each particle. In these situations, the detection system will fail to respond properly because of erroneous measurement.

It is known that it takes a time period of approximately $4\tau$ to collect 98% of the scintillation light from each radiation excitation. Thus, if the next event arrives at time $t>4\tau$, the pile-up-energy error on the next event will be less than 2%. Hence, to keep pile-up error small, it is desirable to minimize the chance that two events (radiation excitations) will occur in a time period less than $4\tau$. Since the time-lapse between two events is a random distribution (i.e., the time-lapse between two events is a random variable) centered about the "average arrival time", it is generally practiced in the prior art to operate the detector so that the "average arrival time" is $10\times(4\tau)=40\tau$, to lower the random chance of having two events coming closer than $4\tau$. With this 10× "head-room", the probability that two events will come closer than $4\tau$ would be approximately 10% (using Poisson statistics). The head-room factor as a function of pile-up percentage is shown in Table 1 below:

TABLE 1

| HEAD-ROOM FACTOR AND PILE-UPS | | | | |
|---|---|---|---|---|
| Head-Room Factor | 5 times | 10 times | 15 times | 20 times |
| pile-up/total (%) | 18% | 10% | 6.5% | 5% |

Thus, a 10× head-room is a reasonable choice, and is generally practiced in the prior art. When coupled with a $4\tau$ light-collection time (system dead-time), such a prior art detector provides a measured-energy error (due to pile-up) of less than approximately 2% for approximately 90% of the time, and an energy measurement error (energy resolution) greater than 2% for approximately 10% of the time. This minimum 10× head-room ($40\tau$) timing requirement means that the maximum detection-rate should be less than $1/(40\tau)$ for the scintillation detector.

The present invention permits a scintillation detector system to operate at a much higher event-rate (count-rate) by obviating the 10× head-room factor without pile-up. The present invention maintains a greater event-rate with little sacrifice in the total amount of scintillation light collected, specifically at a 10 times higher radiation flux with little or no sacrifice in measurement accuracy. If the fraction of scintillation light collected can be reduced (i.e., if a user is willing to compromise measurement accuracy), the present invention allows the detector to count at count-rates approximately twenty times greater than conventional methods.

SUMMARY OF THE INVENTION

The present invention includes an apparatus for signal pile-up prevention, comprising a delay circuit for receiving, holding, and passing an incoming signal; a computation circuit for determining a weighted value of the incoming signal; a sampling circuit for receiving the weighted value. The sampling circuit passes the weighted value (which may be passed to an A/D converter) upon receipt of a triggering signal, which corresponds to receipt of a next incoming signal at a trigger circuit. In an exemplary embodiment, the computation circuit may comprise an amplifier, an integator, and an adder. In an exemplary embodiment, the weighted value is a sum of an integrated value and an instantaneous value, and may be a substantially constant value.

An apparatus according to the present invention may also include a smoothing circuit connected to the circuit adapted to receive the incoming signal. The apparatus may also comprise a residual subtraction circuit for reducing the weighted value by a residual signal value. The sampling circuit discharges said weighted value upon input of the triggering signal.

The present invention may be used in connection with nuclear medicine applications, such as a PET or gamma camera, and may be used to determine both energy and position information. Such an apparatus comprises a plurality of delay circuits, a plurality of computation circuits, and a plurality of sampling circuits, wherein each of the delay circuits receives a different incoming signal from a different output of a gamma camera. The delay circuit, computation circuit, and sampling circuit comprise a pile-up prevention circuit.

Particular embodiments will comprise a plurality of pile-up prevention circuits, and may include a digital signal processor and fast trigger connected to each of the pile-up prevention circuits. Such an embodiment may also comprise an inter-zone detection circuit connected to the fast trigger and a multi-zone-trigger processor connected to said inter-zone detection circuit, capable of centroid averaging. An exemplary embodiment may have a plurality of fast triggers.

A method for preventing signal pile-up according to the present invention may comprise: delaying an incoming signal for a preselected time prior to passing the incoming signal; computing a weighted value of the incoming signal; and sampling the weighted value upon receipt of a triggering signal from the next radiation particle, thereby preventing signal pile-up. Computing may include amplifying the incoming signal to obtain an amplified signal, integrating the incoming signal to obtain an integrated signal, and adding the amplified signal and integrated signal to obtain the weighted value. This method thereby creates a variable signal collection time.

Another method according to the present invention may determine position and energy information of incoming signals without pile-up. Such a method may include: delaying at least one prenormalized position signal and a total energy signal; computing a weighted value for each prenormalized position signal and the total energy signal; sampling the weighted value for each prenormalized position signal and the total energy signal, upon receipt of a triggering signal from the next radiation particle. In an exemplary embodiment, the prenormalized signals and the total energy signal may be corrected by subtracting remnant values of all previous signals.

In yet another aspect, the present invention comprises an apparatus for dynamically detecting energy of each one of a plurality of incoming signals received from a detector, without pile-up of previous incoming signals, including: a delay circuit connected to receive an incoming signal from the detector and to pass the incoming signal from an input to an output of the delay circuit after a time delay; a trigger circuit connected to receive the incoming signal from said detector, and for generating a triggering signal upon receipt of a subsequent incoming signals at the trigger circuit; a computation circuit connected to the output of said delay circuit for determining a weighted value of the incoming signal; a sampling circuit connected to receive the weighted value from said computation circuit, and for passing the weighted value from an input to an output of the sampling circuit upon receipt of the triggering signal; and a residual subtraction circuit connected to the output of said sampling circuit, for subtracting a residual signal value corresponding to a residual weighted value of previous incoming signals, and for providing an output signal corresponding to the energy of the incoming signal.

Another aspect of the present invention comprises an apparatus connected to a gamma camera for detecting position and energy information of each one of a plurality of incoming signals received by the gamma camera, without pile-up of previous incoming signals, including: a first delay circuit connected to receive a first incoming signal from the gamma camera, and for passing the first incoming signal from an input to an output of the first delay circuit after a first time delay; second and third delay circuit arranged like the first delay circuit to receive, delay, and pass, second and third signals; a trigger circuit connected to receive the third incoming signal from said gamma camera, and for generating a triggering signal and a timing mark upon receipt of a next third incoming signal at the trigger circuit; first, second and third computation circuits, each connected to receive an output of a respective one of the first, second, and third delay circuits, and for determining a respective weighted value for each of the first, second, and third incoming signals; first, second and third sampling circuits, each connected to receive a respective one of the first, second, and third weighted values, and for circuits passing the respective weighted value upon receipt of the triggering signal; and a digital signal processor connected to receive the first, second, and third weighted values, and for subtracting residual signal values corresponding to residual weighted values of previous ones of the incoming signals, and for providing an output signal corresponding to a position value of the first and second incoming signals and an energy value of the third incoming signal.

Another aspect of the present invention resides in a method of obtaining energy information for each one of a plurality of incoming signals received from a detector, without signal pile-up, comprising the steps of: delaying an incoming signal for a preselected time; computing a weighted value of the signal after the preselected time; sampling the weighted value upon receipt of a subsequent signal; and subtracting a residual signal value from the weighted value to obtain the energy information. The residual signal value may correspond to a residual weighted value of at least one previous incoming signal, thereby preventing signal pile-up.

Yet another aspect of the present invention resides in a method of determining position and energy information of a plurality of incoming signals from a detector without pile-up, comprising the steps of: receiving a first and second prenormalized position signal and a total energy signal from the detector; delaying the first and second prenormalized position signals and total energy signal for a preselected time, computing a weighted value for each of the first and second prenormalized position signals and total energy signal after the preselected time; and sampling the weighted value for each of the first and second prenormalized position signals and total energy signal upon receipt of a subsequent first and second prenormalized position signals and total energy signal.

The methods of the present invention may be used to operate gamma-cameras (or other radiation detectors) in very high count-rate situations. The present invention includes the following features: (a) no compromise in measured energy-resolution in low count rates; (b) count recoveries and accurate energy measurement even for gamma-rays within a pile-up involving multiple gamma-rays; (c) optimal scintillation-light collection in very high count-rate situations; and (d) ability to merge with a multi-zone architecture to further increase count-rate capability. The present invention includes algorithms that apply to all triggering gamma-rays (it is to be understood that although gamma-rays are discussed herein, the present invention applies to all types of radiation detectors), for extracting the correct energy and position of every triggering gamma-ray.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIGS. 12A–12B are graphical comparisons of energy spectra of count-rates of prior art methods (FIG. 12A) and methods according to the present invention (FIG. 12B).

FIGS. 13A–D are graphical representations of energy spectrum of an apparatus according to the present invention at very high count-rates.

FIG. 14 is a graphical representation of energy resolution (percentage error) as a function of count-rates of prior art methods and methods according to the present invention.

FIG. 15 is a graphical representation of detected count-rates as a function of true count-rates of prior art methods and methods according to the present invention.

FIG. 16 is a graphical representation of energy spectrum of a delay line pulse clipping method.

FIGS. 17A–F are graphical representations of energy spectrum of a $^{99m}$Tc source with and without remnant subtraction.

FIG. 18A is a representation of a Monte Carlo result according to the present invention.

FIG. 18B is a representation of a Monte Carlo result of a pulse clipping method.

FIG. 18C is a representation of a Monte Carlo result of a conventional fixed integration method.

DESCRIPTION OF ILLUSTRATIVE EMBODIMENTS

Figure 1:
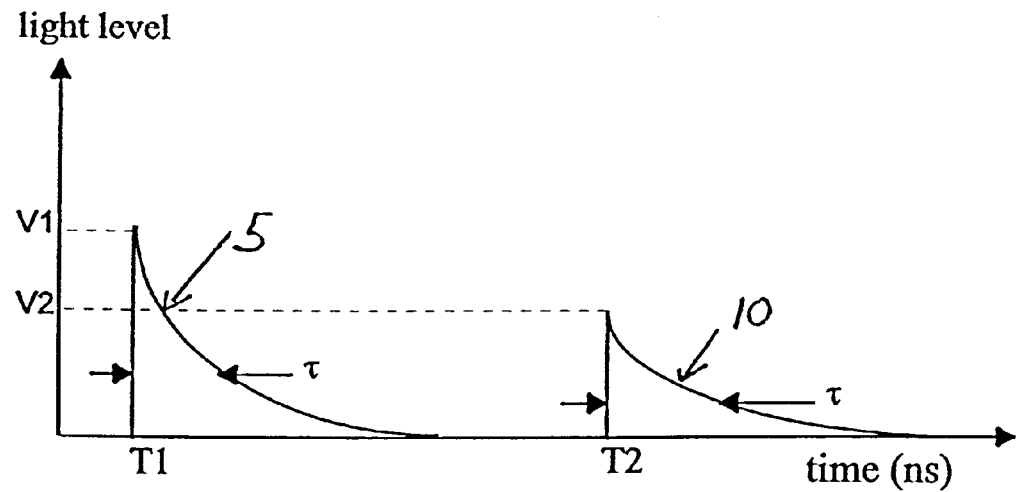
FIG. 1 is a graphical representation of scintillator light output of gamma rays over time.
Figure 2:
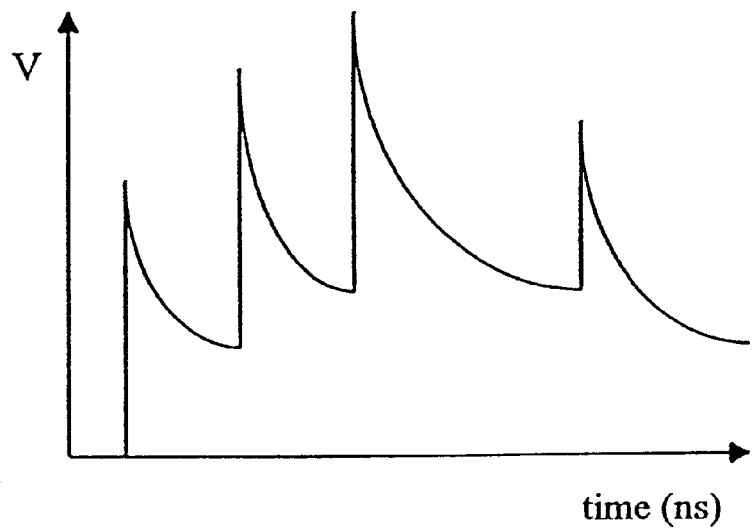
FIG. 2 is a graphical representation of scintillator light output of a plurality of radiation particles having pile-up.

The present invention in a broad aspect comprises a dynamic pile-up prevention technique for increasing the count-rate capability of scintillation detectors. In one embodiment, a NaI(T1) scintillator may be used to illustrate the method. Although NaI(T1) scintillators are discussed herein, the present invention is applicable to other detectors, such as BGO, GSO, LSO, plastic, and CsI. The dynamic pile-up technique of the present invention has a variable detector signal collection time (deadtime), whereas conventional systems typically have a fixed deadtime of 1 $\mu$s ($4\tau$) for NaI(T1) scintillators. The reason that 1 $\mu$s is generally used as a fixed deadtime is that the scintillation light from a NaI(T1) scintillator decays exponentially with a time constant of 0.24 $\mu$s. Thus, approximately 98% of the light is collected in a 1 $\mu$s signal-collection time. Hence, energy measurement error (energy resolution) is minimized.

From Poisson statistics, if a system is counting at a rate of $R=10^6$ counts per second (cps) and if the signal integration (collection) time is 1 $\mu$s, the fraction of non-pile-up counts are only $e^{-R\tau}=37\%$. Hence, approximately $\frac{2}{3}$ of the counts are pile-up events. Though shortening the signal collection time below 1 $\mu$s would improve the fraction of nonpile-up counts, it would also cause two problems. First, shortening the time could increase energy resolution or error (good or small energy resolution is needed to reject scatter noise), as energy resolution is inversely proportional to the square root of light collection. Second, even if the collection time is shortened electronically, scintillation light continues to be emitted by the detector from previously detected gamma ray particles. These remnant signals would be added erroneously to the signal of the following gamma ray particle.

Position sensitive detectors with Anger decoding algorithms are used in SPECT cameras and PET cameras (NaI (T1), BGO and LSO systems) to reduce production costs. One drawback of Anger detectors is lower detection rates because all the photomultipliers (PMT's) involved in the localization of an incident event will be engaged in signal collection for a fixed time period, thereby inhibiting the detection system to process a second event incident within this time period. From energy and spatial resolution considerations, a fixed signal-collection time period of $2\tau_s$ to $3\tau_s$ is preferred, where $\tau_s$ is the scintillation decay-time constant. Due to the random distribution of the time lapse between two events, the average time lapse between two events should be 10 times the signal collection time ($20\tau_s$–$30\tau_s$) to reduce the probability of signal pile-up to 10%. For NaI(T1) and BGO detectors, this limiting average time lapse would be 5–9 $\mu$s, which corresponds to a maximum count rate of 110–200 thousand-counts/sec (Kcps) per crystal or crystal-block, which has been the maximum count-rates of most gamma-cameras and BGO block detectors for many years. However, for certain applications, higher operating count-rates are preferred.

Recently, with the advent of coincidence positron imaging gamma-cameras, the need for increasing camera count rates has become more immediate. Currently, two approaches are used to increase gamma-camera count rates:

(a) a dynamic integration method which integrates the first signal until a next event (pile-up) arrives. An estimated signal supplement is then added to the first pulse to correct for the signal collection deficit, and the same correction signal is subtracted from the next pulse to correct for the remnant light from the present pulse (Lewellen et al., 1989). This method is relatively simple for a two event pile-up, but is more complicated for a multiple-event pile-up, where an additional circuit is needed for each higher multitude of pile-up.

(b) a delay-line pulse-clipping (DLPC) method, which has been applied to NaI(T1) PET cameras (Karp et al., 1986). This technique has been adapted recently to coincidence imaging gamma-cameras. Generally, the DLPC technique reduces the scintillation pulse width to τ (from 3τ), which increases the maximum camera count rates by about 3 times. An advantage of this method is that it can be integrated into a multi-zone architecture, which splits a NaI(T1) crystal into multiple pseudo-independent zones (as if having multiple pseudo-independent crystals) for increasing the maximum camera count rates further. It is known that the DLPC technique (Muehllenhner and Karp, 1986; Karp et al., 1986; Tanaka et al., 1979; Miyaoka et al., 1996b) may be used to alleviate the remnant signal problem, but such a technique does not remedy the degraded energy resolution problem. Furthermore, this technique only defers the onset of pile-up to a moderately high count rate.

Another proposed approach disclosed in U.S. Pat. No. 5,430,406, which is hereby incorporated by reference, uses a dynamic approach to obtain a weighted sum of the instantaneous signal and the integrated signal to depict the energy for the first event in a two event pile-up. The second event in this two-event pile-up was only used for detecting a pile-up condition to process the first event, and this second event is not processed further for recovery attempts. Hence, this method may maintain a good spectra at moderately high rates when the most of the pile-ups are two-event pile-ups, but the count-loss will be high due to the loss of the second event. Second, it can be shown theoretically that the weighted sum is generally not equal to the energy of an impinging event (See Appendix), because it also includes the remnant light from all previous events. The weighted sum is only equal to the event energy when the first event in the two-event pile-up is not a pile-up on previous events, which is a condition in contradiction with very high count-rate situations, where most events are riding on the signal of one or more previous events. Hence, the errors in this energy measurement method will be large in very high count-rate situations (when many events are part of multiple-event pile-ups), as shown in the following table derived from Poisson's statistics for NaI(T1) for the probabilities of multiple-event pile-ups within 1 μs:

TABLE 2

PILE-UP FRACTION AS A FUNCTION OF COUNT-RATES

|  | no pile-up | 2-event pile-up | 3-event pile-up | 4-event pile-up | 5-event pile-up | 6-event pile-up | 7-event pile-up |
| --- | --- | --- | --- | --- | --- | --- | --- |
| 1 Mcps | 0.37 | 0.37 | 0.18 | 0.06 | 0.02 | 0 | 0 |
| 2 Mcps | 0.14 | 0.27 | 0.27 | 0.18 | 0.09 | 0.04 | 0.01 |
| 4 Mcps | 0.02 | 0.07 | 0.15 | 0.2 | 0.2 | 0.6 | 0.1 |

Figure 3A:
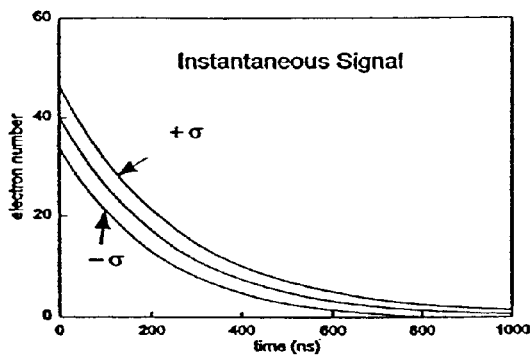
FIG. 3A is a graphical representation of exponential decay of a radiation particle over time.
Figure 3B:
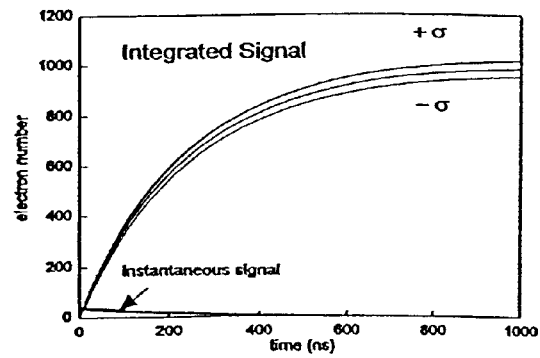
FIG. 3B is a graphical representation of total integrated energy from a radiation particle.

The present invention provides a new approach for preventing signal pile-up, namely, a hybrid signal processing method based on several concepts. It is known that after a scintillation crystal detects a gamma ray, the light output decays exponentially. This signal is illustrated in FIG. 3A, together with its one-standard-deviation (±σ) error boundaries. Initially, about 40 electrons per 10 ns period are generated from a 140 KeV energy deposition (from $^{99m}$Tc). The total integrated signal over a period of 1 μs is approximately 1000 electrons from this 140 KeV energy deposition event, as shown in FIG. 3B. For a scattered gamma ray of 70 KeV energy deposition, the initial signal would be 20 electrons per 10 ns period, and the total integrated signal would be 500 electrons. Although these numbers are specific for gamma rays detected by a NaI(T1) scintillation detector, the same general principles, and the general curves shown in FIGS. 3A and 3B apply to other radiation particles and other radiation detectors. Thus, both the instantaneous signal and the integrated signal may be used to determine the detected gamma energy. However, the percentage-error is much less with the integrated signal collected over 1 μs, as shown in FIG. 3B. For this reason, only the integrated signal technique is used traditionally.

The present invention includes a hybrid signal processing technique that uses both the instantaneous signal and the integrated signal together to help derive the radiation energy, since both signals contain radiation energy information.

Figure 4A:
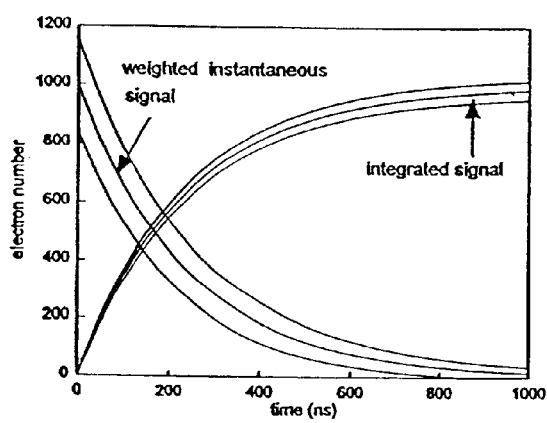
FIG. 4A is a graphical representation of a weighted instantaneous and integrated signal of a radiation particle according to the present invention.

In an exemplary embodiment, the instantaneous scintillation signal from the photomultiplier-tube (PMT) may be smoothed with a filter, for example a 10 ns time-averaging RC-filter. This smoothed instantaneous signal and the integrated signal are shown in FIGS. 3A and 3B. The smoothed instantaneous signal is amplified to the equivalent of 1000 electrons at time zero, and this amplified instantaneous signal is summed with the integrated signal (unamplified) as shown in FIG. 4A. Although the particular embodiment described herein amplifies this signal to a certain level of 1000 electrons, it is to be understood that the smoothed instantaneous signal may be amplified to various levels, depending upon the type of radiation and detector. In certain embodiments, the smoothed instantaneous signal need not even be amplified.

The resultant weighted-sum signal of the instantaneous signal and the integrated signal is a constant and is always a measure of the radiation energy if the event is not a pile-up on previous events, regardless of when the sum-signal is sampled. In an exemplary embodiment, the sampled signal amplitude may always be 1000 electrons, which is equivalent to a 140 KeV energy deposit. The weighted sum is constant in time, because the amplified (weighted) instantaneous signal decays as $\tau(E_o e^{-t/\tau}/\tau)=E_o e^{-t/\tau}$ (a property of NaI(T1) and other scintillators), and the integrated signal increases as $E_o(1-e^{-t/\tau})$, the mathematical property of integrating an exponential function. Thus, the weighted-sum is independent of the time at which the signal is sampled by the components of the present invention. Combining the instantaneous signal and the integrated signal derives the weighted sum according to the following equation.

$$\text{Weighted Sum} = E_o e^{-t/\tau} + E_o(1-e^{-t/\tau}) = E_o \quad (1)$$

Figure 4B:
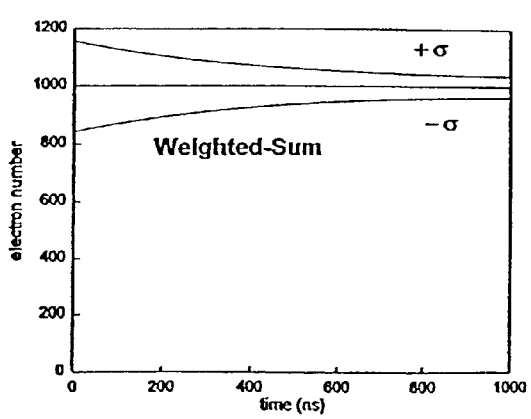
FIG. 4B is a graphical representation of a weighted sum of an instantaneous signal and an integrated signal of a radiation particle according to the present invention.

Given this equation for the weighted sum signal, it can be seen that at certain times, more of the signal will be derived from the instantaneous signal, while at other times, more of the signal will be derived from the exponential signal. If the weighted sum is sampled at earlier times, the variance of the measurement is higher, because more information weight is given by the instantaneous signal, as shown in FIGS. 4A–B. If the sum signal is sampled at 1 μs, the sum converges to that of the integrated signal with a smaller variance, as shown in FIG. 4B.

In the present invention, if there is no next gamma ray detected within the conventional integration time period, for example, 1 μs, the sum signal acquired in the duration of the present event is sampled. If a next gamma ray arrives within 1 μs, the signal (sum) in the duration of the present gamma ray is sampled immediately before the scintillation signal of the next gamma ray reaches the signal measurement circuit. Hence, the measured signal sum relating to the present gamma ray excludes the erroneous pile-up signal from the next gamma ray. However, the signal sum may still contain signals from previous events.

Figure 19A:
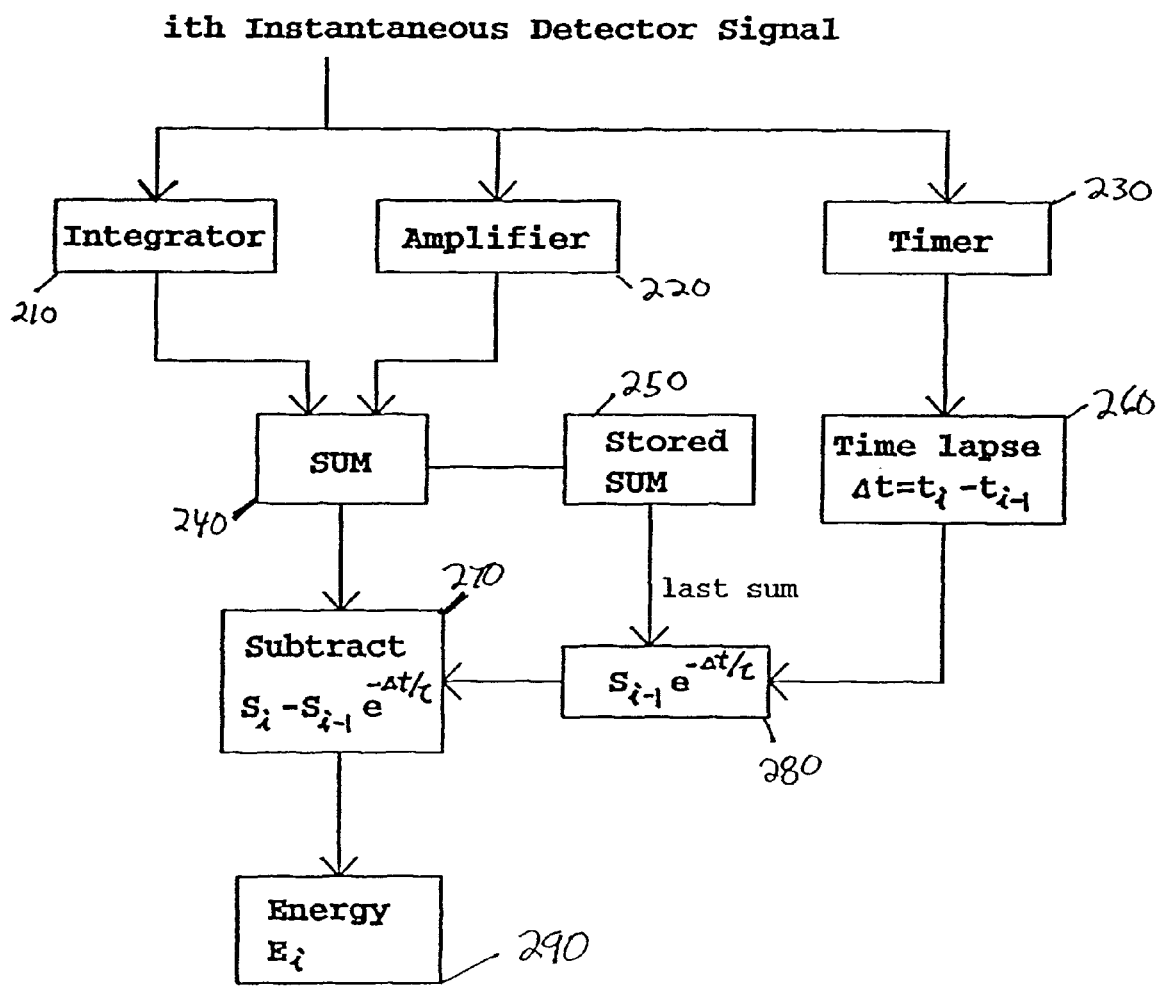
FIG. 19A is a flow chart of an exemplary method according to the present invention.

A flow chart of an algorithm according to the present invention is shown at FIG. 19A. As shown in FIG. 19A, a detected signal is integrated in step 210, is amplified in step 220, and causes a trigger signal in step 230. The integrated value of the detected signal and the amplified value of the detected signal are summed in step 240. The summed value is stored in step 250 and is sent also to the residual subtraction circuit for use in processing.

In addition, the trigger signal from step 230 is sent to determine time lapse between the present detected signal and the previous detected signal in step 260. The sum of the previous detected signal is multiplied by an exponential of the time lapse in step 280. This value is then subtracted from the present detected signal sum value in step 270. The output of step 270 is the detected energy signal $E_i$, as shown in step 290.

Figure 5A:
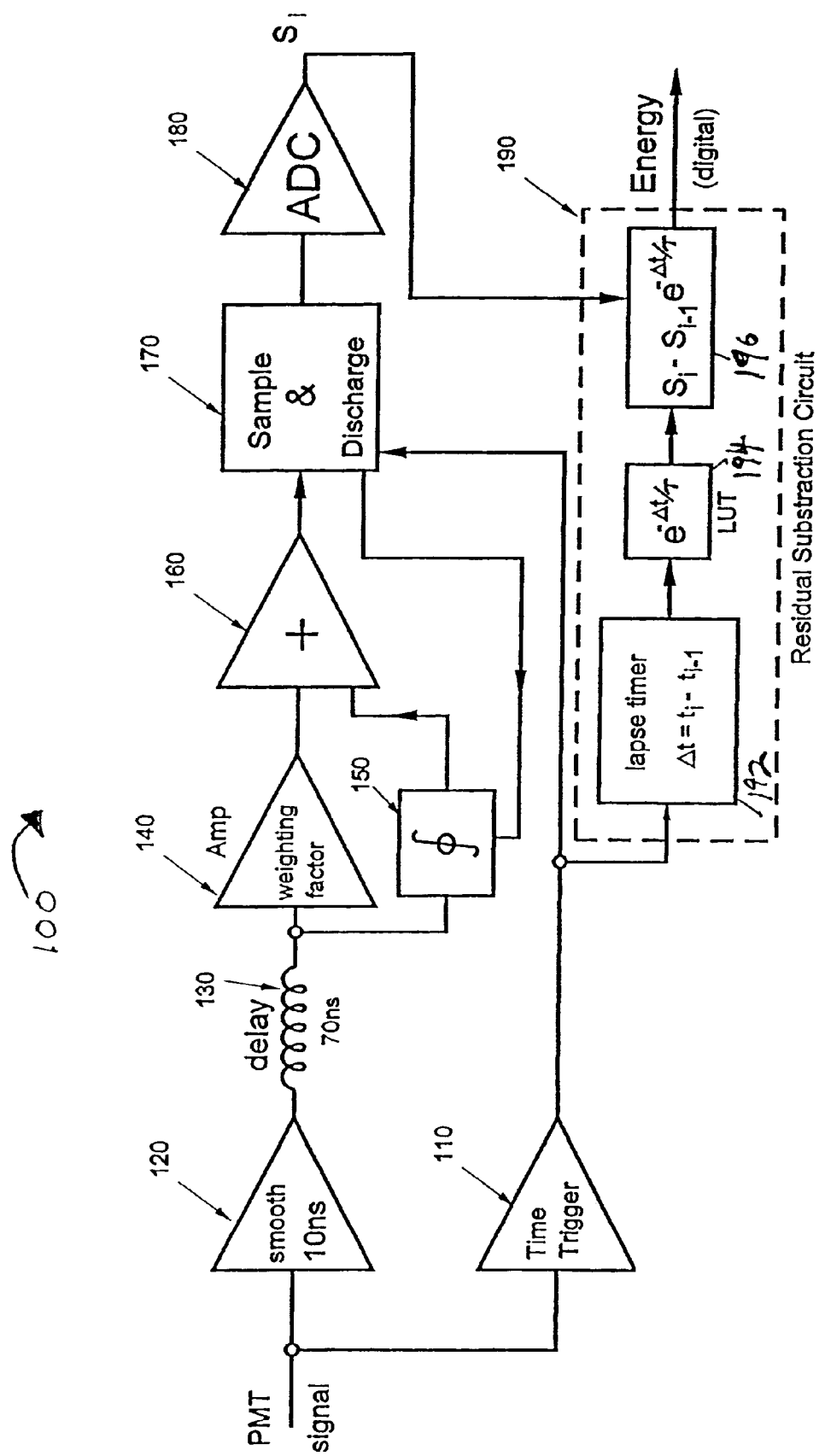
FIG. 5A is a block diagram of an exemplary embodiment of the present invention.

A block diagram of an exemplary embodiment of the present invention that implements this technique is shown in FIG. 5A. As shown in FIG. 5A, the exemplary pile-up prevention circuit 100 receives electrical signals from a photosensor (not shown in FIG. 5A) connected to the input of the circuit. The pile-up prevention circuit (PPC) 100 includes a timing trigger 110, which provides a signal to the sample and discharge control circuit 170 and residual subtraction circuit 190 upon receipt of a signal. In an exemplary embodiment the timing trigger 110 may be a simple threshold discriminator or a delay-line clipping discriminator, which minimizes retriggering by the remnant signal of the same particle. Alternately, the timing trigger 110 may be another appropriate triggering device, for example, a Schmitt trigger. PPC 100 also includes a smoothing circuit 120 to smooth the received signal. In an exemplary embodiment, the smoothing circuit 120 may be a filter, such as a low-pass RC filter or a slow amplifier. Further, in certain embodiments, a smoothing circuit may not be necessary. The smoothed signal passes to a delay circuit 130, which provides a desired delay to the signal before application to the calculation portion of the circuit. In an exemplary embodiment, the delay circuit 130 may be a delay cable or analog delay line integrated circuit. The delay circuit 130 may provide for a delay of between about 1 to 100 ns, and more preferably between about 5 to 50 ns.

As shown in FIG. 5A, the calculation portion of PPC 100 includes amplifier 140, integrator 150, and adder 160. The amplifier 140 amplifies the smoothed signal, thereby providing a weighting factor to the signal. As discussed above, in an exemplary embodiment the amplifier 140 amplifies the signal to 1000 electrons. In appropriate embodiments, an amplifier may not be necessary. The integrator 150 performs an integration of the signal over the exponential decay of the signal. The outputs of the amplifier 140 and integrator 150 are input into the adder circuit 160, which develops the sum of these signals. The resultant sum is forwarded to sample and discharge control circuit 170.

In an exemplary embodiment, the sample and discharge control circuit 170 may be comprised of a register or the like, and a control circuit, such as a fast analog switch, FET transistor, or the like. Upon a signal by time trigger circuit 110, the sample and discharge control circuit 170 passes the resultant sum to analog to digital converter (ADC) 180. The ADC 180 converts the sum to a digital signal, which is then forwarded as the weighted-sum signal to the residual subtraction circuit 190, which subtracts any remnant signal from previous radiation events.

As shown in FIG. 5A, the residual subtraction circuit 190 includes a lapse timer 192, which determines a $\Delta T$ (or time difference) corresponding to the time between receipt of two detected signals. The residual subtraction circuit 190 also includes a look-up table 194 that determines an exponential value based on the time difference. This exponential value is then multiplied by the previous sum signal $S_{i-1}$ (not shown). Finally, a subtractor 196 subtracts this remnant sum signal from the sum signal $S_i$ relating to the present detected signal to thereby output a digital signal $E_i$ corresponding to energy value of the present signal.

After sampling, the sample and discharge control circuit 170 discharges the output of the integrator 150 to zero immediately by sending a control signal upon receipt of the signal from the timing trigger 110 to a capacitor and switch (not shown) associated with the integrator 150.

In operation, the timing trigger 110 senses the arrival of the initial burst of scintillation electrons from any gamma ray. Immediately, time trigger 110 sends a signal to the sample-and-discharge control circuit 170 to sample the weighted sum of the previous gamma ray and pass the sum signal to the ADC 180. Since the timing trigger 110 has no delay, whereas the sum signal processing branch is delayed (in an exemplary embodiment, the delay may be between about 1 and 100 ns, and more preferably be between about 5 and 50 ns) with a delay circuit 130, the weighted-sum signal is sampled before the arrival of the energy signal from the next gamma ray. The delay is used to ascertain that the weighted sum of the present event is sufficiently discharged before the next event enters the integrator 150.

Hence, pile-up of the next signal onto the present is prevented, and the weighted sum will not contain the energy of the next gamma ray. The delay also provides enough time delay for the sample-and-discharge control circuit 170 to discharge (to zero) the previous integrated signal from the integrator 150 before the arrival of the next signal, which prepares the integrator 150 for the next signal. The discharge avoids pile-up of the old integrated signal onto the new integrated signal.

Figure 5B:
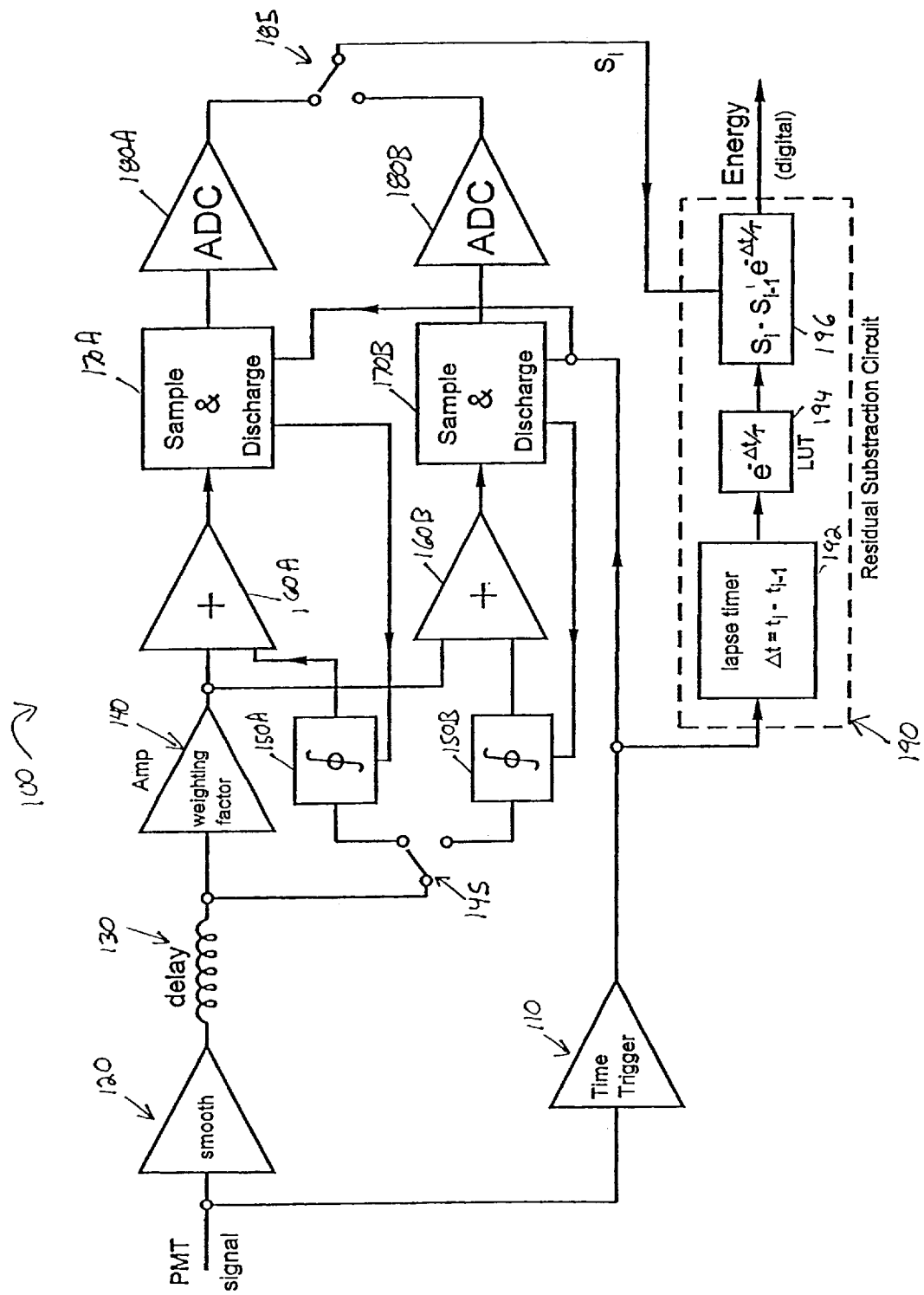
FIG. 5B is a block diagram of another exemplary embodiment of the present invention.

Since it takes a finite time for the electrical-charge output of the integrator 150 to be fully discharged to zero, especially if the previous event has high energy, this discharging time is the ultimate practical limit (processing dead-time) restricting the maximum count-rate performance of the present invention. In an exemplary embodiment, as shown in FIG. 5B, a dual-integrator design ("ping-pong") may be used as the integrator, with each integrator 150A and 150B taking turns in processing each consecutive event as follows: when a present event is detected, the circuitry will be switched via switch 145 to integrator 150A to integrate the signal of the present event; when the next event is detected, integrator 150A will stop integrating the present event and the integrator output will be sampled. At the same time, the circuits will switch the second signal to integrator 150B for integration without waiting for integrator 150A to be discharged. Hence, integrator 150A is discharged in this idle duty cycle when the integration of the next event is performed by integrator 150B. This will provide more than enough time for the integrator 150A to discharge fully.

When a third event is detected, the signal will be switched back to integrator 150A, which is fully discharged, for integration, and the integrator 150B is sampled and discharged at its leisure. Hence, with a dual-integrator "ping-pong" design, the discharging dead time is eliminated (to increase processing count-rate) and the error in energy measurement due to incomplete discharge is also eliminated.

As shown in FIG. 5B, there may be two independent channels, each of which may comprise an integrator 150A or 150B, an adder 160A or 160B, a sample-and-discharge circuit 170A or 170B, or an ADC 180A and 180B, together with an input switch 145 and an output switch 185 for selecting the processing-channel. Each channel takes turn to process the next incoming event. In other embodiments, there may be more than 2 channels present. This also provides an idle duty cycle for the integrators in each channel to be sampled and fully discharged. This dual-channel design also allows the use of a slower ADC (50% slower) to digitize the signals thus lowering cost.

The digital remnant subtraction circuit 190 may include a digital look-up-table (LUT) for determining the remnant scintillation energy (from all preceding gamma rays) that the scintillator is still emitting after the arrival of the latest gamma ray. Specifically, the remnant subtraction circuit 190 may include a register (not shown) to store a previous weighted sum, a LUT 192 for generating an exponential term, and a digital multiplication IC (not shown). The input to the LUT is the trigger-time of the present and the preceding gamma ray (actually, their time difference Δt). The digital energy output of the remnant subtraction circuit 190 is thus the pile-up free energy ($E_i$) of the detected gamma, $$E_i = S_i - S_{i-1} e^{-\Delta t/\tau} \qquad (2)$$

where $S_i$ is the weighted-sum relating to the present gamma ray, $S_{i-1}$ is the weighted sum relating to the preceding gamma ray, and Δt is the time interval between arrival of the present and the preceding gamma ray. $S_i$ and $S_{i-1}$ include the remnant signals from all preceding gamma rays. This is an exact equation, regardless of how many multiple pile-ups exist in each sum signal (see APPENDIX for the mathematical justification). The correction term and the exactness of this algorithm, being independent of the number of multiple-pile-up remnants still being emitted by the scintillator, are significant consequences of the present invention. Thus, the scintillation detector used in connecting with the present invention permit count-rates that produce 60% multiple pile-ups, since all the remnants from multiple pile-ups can be easily corrected for by equation (2). The present invention processes all incoming events the same way, regardless of whether it is a pile-up onto a previous event or whether there is a pile-up from the next event.

All the components in a circuit according to the present invention are basic required components of conventional detector electronic systems, with the exception of the timing trigger and the residual subtraction circuit. Therefore, the real-time pile-up prevention/correction provided by the present invention is an inexpensive solution to the problems inherent in the prior art. If there is no pile-up, the system converges to a conventional integrating circuit, as the sample and discharge control circuit 170 may be set to pass the resultant sum signal at a time approximately equal to 4τ (i.e., approximately 1 μs for the NaI(T1) detector discussed herein). In case of a pile-up, it correctly measures the energy of all the pile-up gamma rays.

As long as the average time lapse (ΔT) of arrivals between two gamma rays is longer than the average detector integration time (Tc=1 μs), the average fraction of scintillation light collected will not diminish, which means the detected energy resolution will not be compromised. Hence, a NaI (T1) scintillation detector employing the methods and apparatus of the present invention has the potential to count up to $1 \times 10^6$ cps without degrading the average energy resolution. A traditional detector circuit with a deadtime of 1 μs must lower the acceptable count-rate by 10 times, to 100,000 cps, to prevent the random arrival of the next gamma ray within 1 μs of the present gamma ray (Nicholson, 1974). Poisson statistics shows that the non-pile-up fraction is 90% for 100,000 cps, which is why conventional NaI(T1) detection systems cannot count over 100,000 cps. The present invention can count even faster than $1 \times 10^6$ cps with some compromises in energy resolution.

The PPC of the present invention may be adapted for use with many different detectors and imaging systems. For example, the present invention may be used with thyroid probe, position sensitive detectors, or gamma ray detectors which detect neutrons, charged particles and gamma rays.

The conventional integration method (and its equivalent pulse-shaping method) has been the gold standard in the nuclear physics and nuclear medicine field for the past 40–50 years. The present invention is a significant breakthrough. This breakthrough can be applied to many nuclear detection areas, such as nuclear physics and engineering, high energy physics, nuclear medicine, industrial gauging, and oil field down-hole logging, among others. Certain applications will be discussed presently.

Nuclear Medicine Applications

The present invention has special attributes that make it particularly applicable to medical imaging, and especially gamma cameras. When a gamma ray hits a detector in a gamma camera, both energy and position information are needed for creating the image. The energy information discriminates (or qualifies) the useful imaging gamma ray from background gamma rays which have been scattered around in the body being imaged (scattering lowers the gamma energy). When a detected gamma is qualified by its detected energy, the position information locating the point of detection of the gamma ray has to be determined to create a gamma ray map (image).

The pile-up prevention circuit (PPC) of the present invention can determine the gamma ray energy, despite pile-ups. However, the present invention would be less useful for gamma cameras if it could not also determine the gamma ray position in pile-up situations. A particular embodiment of an apparatus according to the present method may be incorporated into a regular gamma camera to determine position information, as well as energy information in a pile-up situation.

This embodiment may be known as a position-energy pile-up prevention (PEPP) algorithm and circuit. This solution is compatible with existing gamma camera electronics. Compatibility is important because it allows the pile-up-prevention circuit of the present invention to be applied to present gamma cameras without major modification to their existing front-end electronics.

A regular gamma camera and its electronics generate five signals of interest for the present invention, namely $X_+$, $X_-$, $Y_+$, $Y_-$, and Z. Z is the energy of the gamma ray. The X-position and Y-position of the gamma ray can be calculated from these five signals, $$X = (X_+ - X_-)/Z \qquad (3)$$

and $$Y = (Y_+ - Y_-)/Z \qquad (4)$$

The prenormalized positions are defined as $X' = (X_+ - X_-)$, and $Y' = (Y_+ - Y_-)$. Hence, the X-position and Y-position can be calculated by a subsequent normalization with Z:

$$X = X'/Z \qquad (5)$$

and $$Y = Y'/Z \qquad (6)$$

In addition to preventing energy pile-ups in scintillator-PMT's, the same PPC circuit may be applied directly to the prenormalized position signals, X' and Y', to prevent pile-ups by generating pile-up-free X' and Y'. The mathematical proof of this property can be found in the APPENDIX. With the realization of this important property, the PPC circuit of the present invention may be connected to the prenormalized positioning signals X' and Y' in a regular camera, as well as the energy signal Z' (a fast instantaneous signal sum of all the PMT's), as shown in FIG. 6, to generate three pile-up-free signals X', Y', and Z' for calculating the energy and position of the detected gamma ray despite multiple pile-ups.

Figure 6:
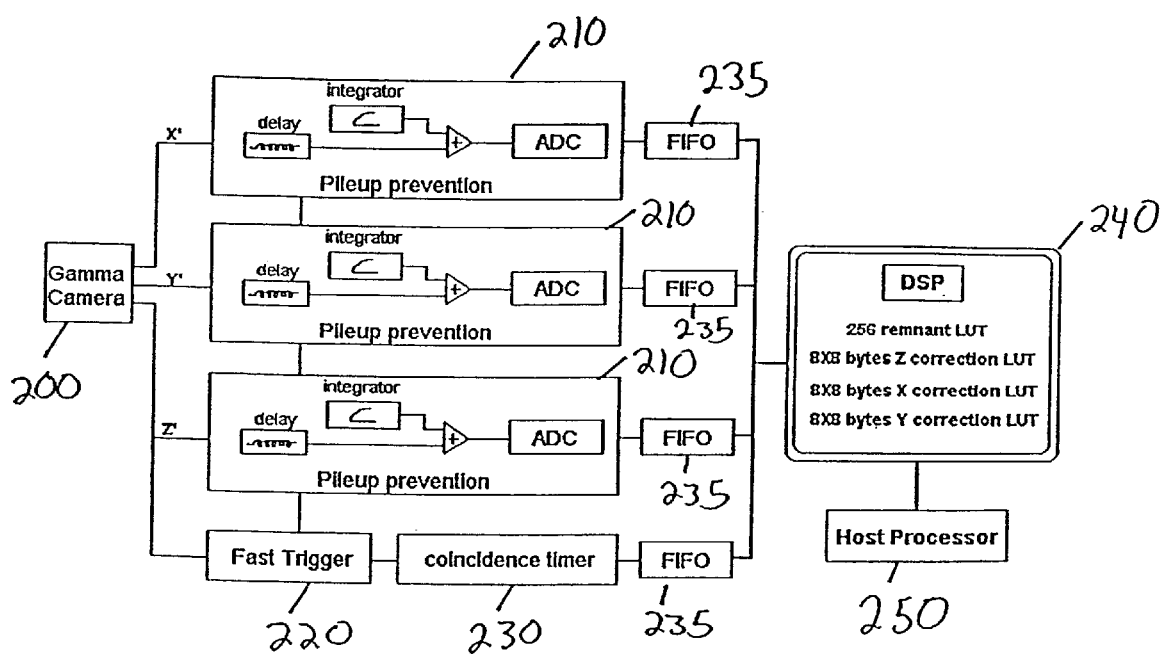
FIG. 6 is a block diagram of an exemplary apparatus according to the present invention.

The system of FIG. 6 includes a conventional gamma camera 200, which develops prenormalized position signals X'and Y', and energy signal Z'. Each of these signals is input into a separate pile-up prevention circuit (PPC) 210. This PPC 210 may be the same circuit as discussed above, in connection with FIG. 5A or 5B, or it may be a slightly modified version (as shown in FIG. 6, certain components of the circuit of FIG. 5A have been deleted for illustrative purposes). First the PPC 210 may not have a time trigger, as trigger signals for this embodiment may come directly from a fast trigger 220, which is input to all of the PPC's 210. This fast trigger 220 is a new addition to a conventional gamma camera. Further, the individual PPC's 210 may not have a remnant subtraction circuit, as all signals output from each PPC 210 may be input into a digital signal processor (DSP) 240. In an exemplary embodiment, the DSP 240 may include the remnant subtraction algorithm for the X', Y', and Z signals. The DSP 240 provides for faster processing. However, in certain embodiments, it may be possible to have the lookup tables within the individual PPC 210 units. The DSP 240 may also include other corrections (energy and distortion corrections) for the X', Y'and Z signals, and X, Y renormalization process.

The system of FIG. 6 also includes a coincidence timer 230, which receives a trigger signal from the fast trigger 220. Upon receipt of the signal, the coincidence timer 230 sends a time clock signal to FIFO's 235, which is transmitted to the DSP 240. This time clock signal is for pile-up remnant subtraction and for coincident timing measurement in positron coincidence imaging (PET).

As discussed above in connection with FIG. 5A, the prenormalized position signals (X', Y') obtained from gamma camera 200 are delayed, amplified, and integrated within the PPC 210. The amplified instantaneous position signals $\tau X'(t)$ and $\tau Y'(t)$ are summed to their integrated position-signal, $\int X'(t)dt$, $\int Y'(t)dt$, respectively, also within the PPC 210. These weighted sums of prenormalized positions are immediately sampled by a fast analog-to-digital converter (ADC) within PPC 210, just before the onset of the next pile-up event. The arrival of the next gamma ray is sensed by the fast trigger 220, which monitors the fast instantaneous total energy output, Z'. After the ADC sampling, the integrator circuit of PPC 210 is immediately discharged so that it can start integrating the position signals coming from the next pile-up gamma ray. Alternatively, there may be two matching integrators taking turns in processing each consecutive signal to allow for an idle duty cycle for discharging the integration to zero. Further, as discussed above, there may be two matching channels of amplifiers, integrators, samplers, and ADC's to handle each successive event to allow the integrators in each channel to discharge to zero.

The fast trigger 220 also marks the arrival time of all gamma rays. The timing mark is generated by a fast clock, which in an exemplary embodiment may be a 250 MHz clock. These arrival times are sent to the DSP 240 for remnant signal subtraction and for positron coincidence detection in PET imaging. The remnants of position signals, generated by the residual light output of all preceding pile-up gamma rays, will be subtracted from the present position weighted-sum in the DSP 240 in FIG. 6 using a LUT that stores the exponential term in the following remnant subtraction operation to determine the remnant position signal to be subtracted from the j-th event:

$$RP_j = SP_{j-1} e^{-(\Delta t)/\tau} \tag{7}$$

and $$Xj_1' = SP_j - RP_j \tag{8}$$

where $SP_{j-1}$ is the last position-weighted sum and $\Delta t$ is the time-lapse between the j and the j−1 position signals. This remnant subtraction strategy automatically subtracts for all higher levels of multiple pile-ups. After the remnant subtraction, the DSP 240 calculates the normalized positioning estimation, X=X'/Z and Y=Y'/Z, where Z is the total energy after remnant correction of the present event. Alternate methods of remnant subtraction may include performing the process within the individual PPC 210 units. The DSP 240 also performs the regular correction processes for linear distortion, field nonuniformity, and regional signal-pulse-height variation, in real time. The host processor 250 is for image display and operator interface.

An apparatus according to the present invention thus decodes the position and energy of each detected event. The fast trigger 220 detects the arrival of an event, and triggers a time-mark output in the coincidence-timer 230 for the event's arrival time. This event-arrival time mark will be used to calculate the prenormalized positions and energy. The calculation may be performed by the DSP 240, where exponential functions may be stored as a look-up-table. The DSP 240 also performs the energy normalization on the prenormalized positions to provide the true position signals. In this processing scheme, all the events (photopeak or true events, and scatter noise events) are included in the processing to calculate all the remnant signals from previous events, and an event's real energy is not known until after processing. Hence, the energy acceptance of an event has to be made after the decoding operation, in/after the DSP 240. If the decoded energy is higher than that of the scatter radiation noise signal, the detected radiation is accepted as a true (photopeak) event. The output of the DSP is thus the pile-up-free, energy-normalized positions (x, y) and gamma-energy (z). Since all data acquisition computers in gamma cameras accept the standard signals of (x, y, z), the proposed processing algorithm and electronic architecture is compatible with existing data acquisition computers. This compatibility is useful to adapt the scheme to existing cameras.

Implementation of the present invention in a conventional camera is very feasible, as shown in FIG. 6. A DSP circuit is standard in most cameras for processing position signals and for distortion correction. Thus, the only additional circuits needed for incorporating the methods of the present invention into a regular camera are the three channels of PPC circuits according to the present invention, a fast trigger-circuit, and a clock, which increase production costs by only a few hundred dollars to achieve a 10–20 times increase in count-rate capability.

Such an increase in count-rate capability would permit or improve the following imaging procedures:

(a) Positron imaging, because it requires the removal of a lead collimator from a gamma camera, which exposes the NaI(T1) detector to a 10-fold or more gamma-ray flux. This forces an injected positron tracer dose to be reduced by 5–10× to prevent significant pile-up in a regular camera. With the present invention, it would not be necessary to reduce the injected dose. The positron image quality would be significantly improved as a result of this 5–10 times increase in positron counts in the image. Imaging time can also be decreased as a result of the increased count-rate capability;

(b) Imaging radionuclide therapy patients to deduce actual radiation dose delivered to tumors and organs so that radionuclide therapy can be improved;

(c) Dynamic first-pass cardiac imaging to study shunts, valves, the right heart and lung;

(d) The use of very short half-life tracers to reduce radiation dose and increase patient throughput;

(e) The use of larger NaI(T1) detectors to reduce scanning time for whole-body imaging;

(f) Acquiring very high count-rate transmission data while the emission data is being collected. In such a scheme, a lower energy gamma source is used for the transmission data; the very high-rate transmission collection is used to minimize the effect of 'down scatter' contamination from the emission gamma. Other improvements in medical imaging would also be produced by application of the present invention.

The present invention also provides for further improvement of the detection rates of a gamma camera. In this embodiment, the camera signals may be split geometrically into 4 or more independent signal processing zones as if four independent cameras existed adjacent to each other. More specific details of such a system are disclosed in U.S. Pat. No. 5,319,204 and, U.S. Pat. No. 5,453,623, the disclosures of which are hereby incorporated by reference. The incorporation of the PEPP (position and energy pile-up prevention) algorithm of the present invention into such a multi-zone design would further increase the count-rate capability of the camera by two or three times.

Multi-zone designs have been proposed and implemented in NaI(T1)-based PET cameras to increase maximum count-rate capability (Muehllehner et al., 1995; Muehllenner and Karp, 1986; Karp et al., 1986; Freifelder et al., 1994). These designs depend on the fact that most of the scintillation light is distributed only to the neighboring 7–9 PMTs.

Figure 7:
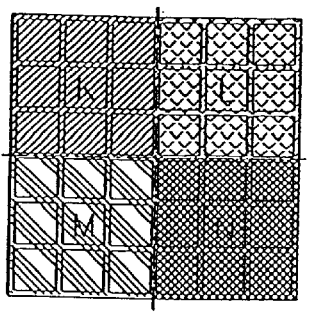
FIG. 7 is an illustration of a PMT configuration that may be used in accordance with the present invention.

For a camera with 36 PMT's (6×6 configuration), the camera may be divided into four identical square zones, identified as K, L, M, N, as shown in FIG. 7. Each zone therefore has nine PMT's (3×3). Each zone may be treated as an independent camera with its own PEPP circuit according to the present invention to correct for pile-ups and image distortions. The nine PMT's in each zone may be grouped into one signal-triggering line. With four zones, there would be four signal-triggering lines, $S_K$, $S_L$, $S_M$, $S_N$. If the first gamma ray is detected in zone K, the PEPP circuit of zone K would be turned on to measure its position and energy. If a second gamma is detected in zone K within the pile-up time, the PEPP circuit would correctly measure the position and energy of both gamma rays.

If the second gamma ray strikes zone L while zone K is processing a prior count, two scenarios may occur. These two scenarios are addressed in detail:

(1) In the first scenario, the gamma rays detected in zone K and zone L are both far from the zone boundaries between K and L, such that there is little light spilled from one zone to the next. Hence, there is little or no signal interaction between the two events to cause positioning errors. Both gamma rays may be processed independently by the PEPP circuit of each zone to obtain the correct energy and position.

Figure 8:
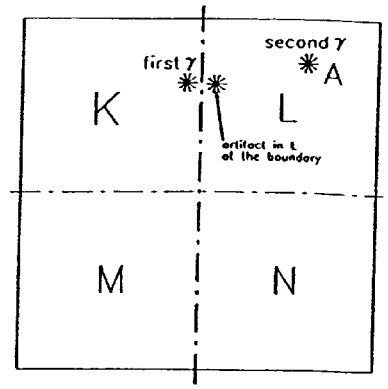
FIG. 8 is a representation of boundary artifact generation.

(2) In the second scenario, the first gamma ray detected in K is so near the K-L boundary that the PEPP circuits in both zone K and zone L are triggered, as shown in FIG. 8. In this case, zone K may decode a valid position, but zone L would decode an artifact-count at the K-L boundary near the event in K, as shown in FIG. 8. When the second gamma hits zone L later, at location A in FIG. 8, the remnant signal of the fictitious count created in the L-PEPP circuit would be subtracted from the signal of the second gamma ray (A), so that there is no interference in determining the position of the second gamma ray. Thus, in this scenario, both the first (K) and second (L) gamma rays would be correctly measured, but an additional artifact count will be created at the K-L boundary.

Figure 9:
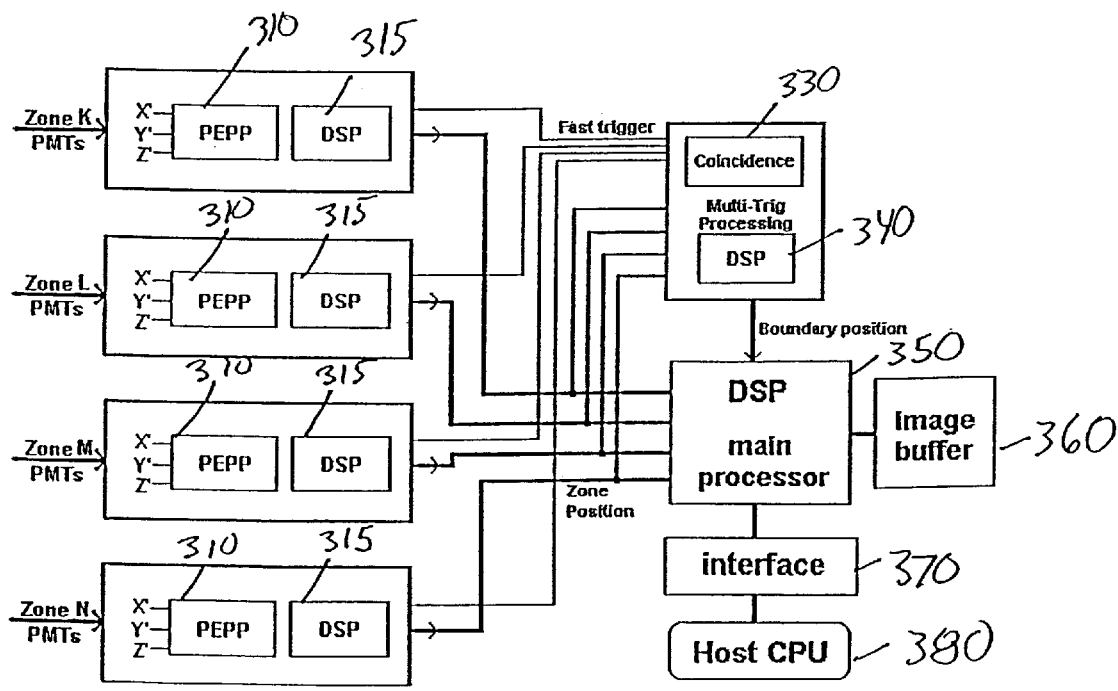
FIG. 9 is a block diagram of an exemplary apparatus according to the present invention.

With these inter-zone light-spill considerations, the processing circuitry for the multi-zone pile-up prevention (MZPP) camera is shown in FIG. 9. As shown in FIG. 9, each zone may have its own PEPP circuit 310. In addition, each zone may have its own DSP 315. These four PEPP circuits may be monitored by an inter-zone coincident detection circuit 330 and a multi-trigger processor 340. The interzone coincident detection circuit receives input from the fast timing triggers of each of the zone PEPP circuits 310. The multi-trigger processor 340 receives zone position signals from each of the zone PEPP circuits 310. In an exemplary embodiment, the processor 340 may be a DSP. The output of processor 340 is input into a main DSP processor 350, which provides information to image buffer 360, interface 370 and Host CPU 380. The main DSP processor 350 serves two functions: (1) it merges the four zone-images into one image, and (2) it performs a final distortion correction for the combined image.

To eliminate the problem of additional artifact counts at a border, the interzone coincidence-triggering circuit 330 (between any two or more zones) may be used to detect the simultaneous triggering of two or more zones caused by an event detected near the boundary. When two or more neighboring zones are triggered by a single event near the boundary, the PEPP circuit 310 in each zone would respond (as originally designed) as if an independent event is detected in each zone by generating their own position signals, $$X_K=(X_{K+}-X_{K-})/Z_K \quad (8)$$

and $$X_L=(X_{L+}-X_{L-})/Z_L \quad (9)$$

Furthermore, the simultaneous triggering of both zones would also activate the inter-zone coincidence circuit 330 which would then feed these two or more independent position signals into multi-zone-trigger processor 340, which performs a centroid averaging for these two or more position signals. Mathematically, this averaging is equivalent to combining the two or more zones and using the regular Anger positioning method over this larger domain, as shown in the following equation:

$$X=(X_K Z_K+X_L Z_L)/(Z_K+Z_L)=\{(X_{K+}-X_{K-})+(X_{L+}-X_{L-})\}/(Z_K+Z_L) \quad (10)$$

This averaged position is stored in the main processor 350 that stores the composite camera image (four zones combined), whereas the individual zone position signals ($X_K$ and $X_L$) are discarded. This method thereby eliminates the boundary-artifact event and also provides a better estimation of the position, since all of the scintillation light emitted would be used for computing the position (including light spilled into the adjacent zone).

Inter-zone light spill also exists in the two high count-rate cameras using a multi-zone design because, as long as a single NaI(T1) crystal is used, light will be distributed from one zone to the next. Technical solutions are readily achievable as indicated by ADAC MCD and UGM SPECT and PET cameras (Muehllehner et al., 1995; Glass et al., 1996; Freifelder et al., 1994). The present invention, using a monitor to detect coincidence triggering of two zones is simple, straightforward to implement, and usable with the pile-up prevention technology of the present invention.

Figure 10:
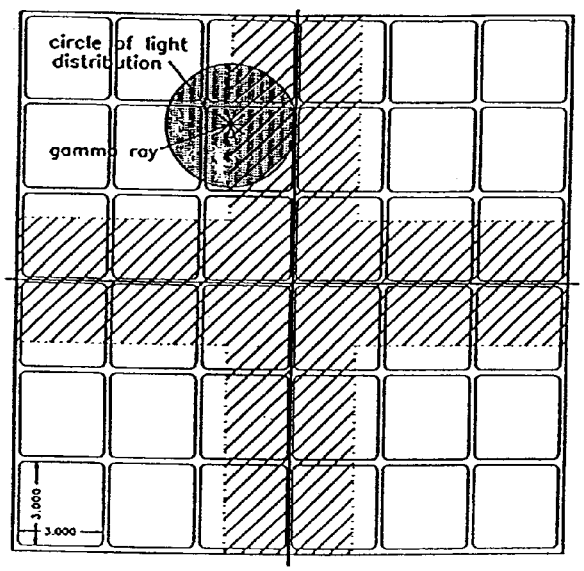
FIG. 10 is an illustration of study results according to the present invention.
Figure 11:
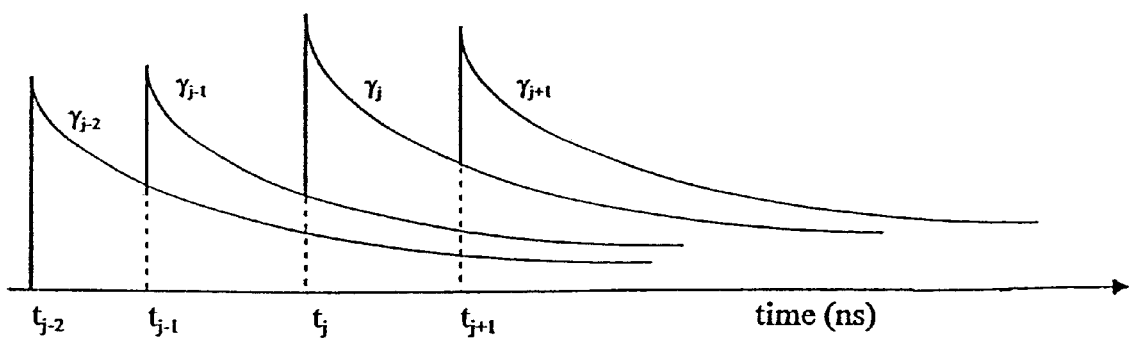
FIG. 11 is a graphical representation of scintillator light output of a plurality of radiation particles having continuous pile-ups.

An increase in detection rates by 2–3 times is expected over the single-zone implementation, if the distribution of the scintillation light is mainly limited to a circle 4.5" in diameter centered on the point of detection. When this light-spread condition is met, only the gamma rays hitting the shaded area shown in FIG. 10 can trigger or affect both zones. Hence, the probability that a gamma ray will hit the independent area is 21/36, while the probability that it will hit the light-spill-over area is 15/36. Thus, the count-rate enhancement obtained by splitting the camera signals into 4 zones is (21/36)×4 or 2.3 times.

Figure 19B:
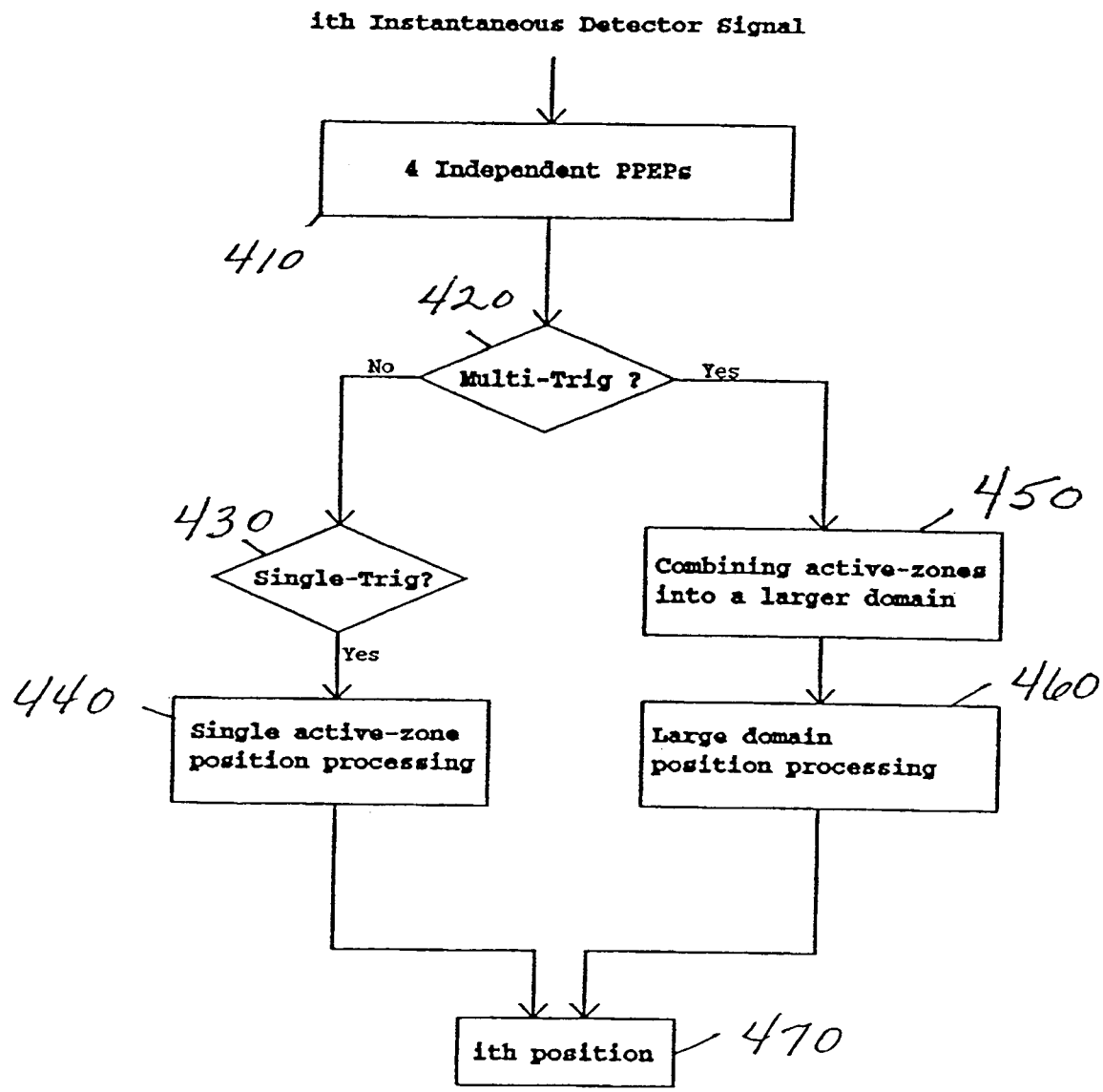
FIG. 19B is a flow chart of another exemplary method according to the present invention.

Shown in FIG. 19B is a flow chart for the method of the present invention relating to this multi-zone pile-up prevention embodiment. As shown in FIG. 19B, an instantaneous detected signal is provided to four independent PEPP's in step 410. Then it is determined whether this signal creates a multi-trigger event in step 420. If it is not a multi-trigger event, control passes to step 430, in which it is determined whether it is a single-trigger event. If it is a single-trigger event, control passes to step 440 and single active zone position processing is performed, as discussed above.

If it is determined that it is a multi-trigger event, in step 450 active zones are combined into a larger domain for processing. Then, the large domain position processing is performed in step 460, as discussed above. The result of either path of this method results in a determination of the true and accurate position of the instantaneous signal in step 470.

Combining the pile-up prevention method and the multi-zone method, the count-rate of a camera according to the present invention may reach 4,000,000–5,000,000 cps. With optimization and further development of the PEPP circuit as discussed earlier, the count-rate may be extended further. Monte Carlo simulation indicates that $2 \times 10^6$ cps is achievable with the pile-up prevention method alone, and a combined count-rate of $2.3 \times 2 \times 10^6 = 4.6 \times 10^6$ cps may be achievable, a significant improvement over the $10^5$ cps achievable in a regular camera.

The present application of scintillation detectors can be divided into four main areas:

(i) industrial gauging, including thickness, level and density gauging;
(ii) surveying, including oil field logging, nuclear reactor monitoring, nuclear fuel cycle monitoring and airport luggage inspection for explosives;
(iii) research applications in nuclear physics, high-energy physics, medicine, and industry; and
(iv) medical uses (gamma cameras, PET cameras, bone scanners, thyroid probes, general purpose probes, monitors, and dosimeters).

A new and potentially important application of the present invention is in airport surveillance to look for plastic explosives in luggage using, for example, neutron activation techniques. The ability to detect radiation 10–20 times faster would allow (a) detectors to be used in a much higher radiation areas to extend the usefulness of the detector system, (b) the ability to count faster would increase the speed of data acquisition to shorten the data collection time, e.g., in an airport bomb surveillance system, a 10–20× stronger neutron source can be used to scan luggage faster, so that luggage scanning times can be reduced by 10–20 times to improve throughput.

In industrial gauging application, the scintillation detector is used in conjunction with radiation sources to measure the quantities or density of materials being processed. For example, while molten cement or molten metal is poured into a container, a nuclear level gauge may be used to stop the pouring process when a specific level is reached. Another example is "thickness gauges" using gamma-ray backscatter detectors in thin-film processing in the plastic and paper manufacturing industry (especially for high-value films such as video-tapes and electronic capacitor films). Quite often, the film to be scanned is manufactured in large-area sheets, and the detectors together with the radiation source must scan the entire sheet. The detector's ability to detect gamma rays at very high count-rate (10–20×) means that a very intense gamma-ray source (10–20×) can be used, which in turns translates to a 10–20× faster data acquisition. Thus, the time spent on the inspection-scanning processes or manufacture-control processes can be reduced by 90%, thereby increasing production rate.

Scintillation detectors are also widely used in radiation monitoring in nuclear reactors, and in oil field borehole logging to survey rock/hydrocarbon structures along the borehole in oil exploration. A faster counting system would increase the information collected or decrease the data collection time, which would lower the cost of data acquisition (oil rig time is very expensive).

Scintillation detectors are also widely used for nuclear applications, for example: (a) reactor monitoring of liquid and gaseous streams to look for isotopes, (b) fuel rod cladding failure, (c) isotope scanning for irradiation fuel to determine power distribution and migration of fission products in the reactor core, (d) reactor fuel fabrication and quality control, (e) spent fuel reprocessing, and (f) management of nuclear waste. Since these nuclear-reactor related detectors are used in very high radiation flux areas, this high count-rate invention is potentially very useful in the nuclear energy business.

In research laboratories, a faster counting detector system is always welcome, as it allows new experiments to be performed. Nuclear-electronics instrumentation companies that market detector electronic modules for research laboratories may wish to add this electronic invention to their catalog.

In medical imaging applications, present gamma cameras are adequate for imaging diagnostic quantities of single photon tracers, but their limited count-rate capabilities introduce image artifacts and count-loss, and degrade image quality when gamma ray flux is high. These situations may occur in:

(a) positron imaging, which exposes the NaI(T1) detector to a 10-fold or more gamma-ray flux, with the removal of the lead collimator from a gamma camera for positron imaging;
(b) imaging radionuclide therapy patients to deduce the actual radiation dose delivered to tumors and organs for improving radionuclide therapy treatment;
(c) dynamic first-pass cardiac imaging to study shunts, valves, the right heart and lung;
(d) the use of very short half-life tracers to reduce radiation dose and increase patient throughput;
(e) the use of larger NaI(T1) detectors to reduce scanning time for whole-body imaging; and (f) acquiring very high count-rate transmission data while the emission data is being collected (the very high-rate transmission collection minimizes the effect of 'down scatter' contamination from the emission gamma).

With this invention, the count-rate capability of gamma cameras can be enhanced by 20–40 times, which would allow (or improve upon) the above useful imaging protocols. The new capability may reduce reliance on the use of PET costing $2,600,000 to purchase and $250,000/yr to operate. Another application of the present invention is for the low-cost, high-resolution PET detection system of PMT-quadrant sharing design, as shown in U.S. Pat. Nos. 5,319,204 and 5,453,623, to compensate for its lower count-rate.

Thus, the present invention will open up new and exciting clinical applications for gamma cameras, which is especially important in today's healthcare environment when clinics must perform more with less money.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

WORKING EXAMPLES

In studies with an exemplary embodiment, the present invention was used in connection with a 3"×4" NaI(Tl) scintillator with a photomultiplier from Ortec Corporation (Oak Ridge, Tenn). This detector was connected to (1) regular detector electronics setup using a pulse-shaping amplifier (0.5 µs shaping time) and a multi-channel analyzer, and (2) to the pile-up prevention circuit ("PPC") of the present invention.

The circuit may be interfaced to a computer. For example, the present invention was connected to a PC computer with a 133 MHz PENTIUM processor and a high-speed input/output board for the studies. The data acquisition software was written with LABVIEW (National Instruments, Austin, Tex.). A $^{99m}$Tc point source (140 KeV gamma ray) in air was used for all the count-rate studies. The pile-up-prevention circuit of the present invention may also be used to measure the number of nonpile-ups, single pile-ups, and multiple pile-ups.

For comparison studies, circuits implementing three methods were setup and tested. The methods included: (i) the pulse-shaping method (500 ns); (ii) delay-line clipping (256 ns); and (iii) the method according to the present invention. The pulse-height spectra, energy resolution and acquired true-count fractions were collected as a function of true-even rates using a $^{99m}$Tc (140 KeV) point source, which decays with a 6 h half-life. This half-life was used to calculate the true-even rate impinging the detector when very high count-rate data were acquired.

A. Example I

The pulse height spectra of $^{99m}$Tc (140 KeV gamma-ray) for the pile-up prevention circuit of the present invention and the pulse-shaping method (500 ns) are shown in FIGS. 12A and 12B. FIG. 12A show results of the pulse-shaping method, and FIG. 12B show results of the present invention. At 50 Kcps, both measured 10.9% energy resolution. At 120 Kcps, the pulse-shaping method (FIG. 12A) started to demonstrate pile-up at the higher energy side and distortion at the lower energy side. Above 200–300 Kcps, the spectra were not usable. The PPC method spectra (FIG. 12B) maintained the spectra shape even at 2 Mcps. This first study demonstrated that the method of the present invention can significantly extend scintillation counting rates. However, the energy resolution was poor at 2 Mcps for this first study. Part of the reason was due to DC-level instabilities because the resistor divider of the photomultiplier (PMT) in the ORTEC probe was AC-coupled and the biasing-current was not designed for such a high count rate (there was no reason to design for such high rates previously because of NaI(Tl) pulse pile-up). Another reason was that the prototype board incorporating the apparatus of the present invention was built on a simple board with holes and the wiring was done with wirewrapping wire. A third reason was that a single integrator was used, which may not have been sufficiently discharged if the last event had a very high energy. Both the PMT divider and the prototype circuit were subsequently improved. Dual integrators and ADC channels ("ping-pong") were provided to assure complete discharge of the integrators. The pulse height spectra were measured again for the method of the present invention, and the energy resolution was significantly improved, as shown in FIGS. 13A–D. Even at 2 Mcps (FIG. 13C), the energy resolution achieved 15% compared to 10.9% at 50 Kcps; part of the reason for this difference is the shorter average signal collection time when the count rate is very high. At lower count rates, the integration time for most pulses were integrated to 1 µs, while at 2 Mcps, the average time-lapse between events was 500 ns which implies that the average signal collection time would be equal to or less than 500 ns.

B. Example II

In a second study, the method of the present invention was compared with a delay-line clipping (DLC) experimental setup (using NIM electronic modules and a 256 ns clipping). The energy resolution results are shown in FIG. 14. At lower count rates, the PPC method had better resolution than the DLC method, while at 2 Mcps the energy resolution was about the same. The study also generated the photopeak-count rates, i.e. the non-pile-up good counts acquired by each method using a narrow energy window, as a function of true-count rates, as shown in FIG. 15. For the method of the present invention at 2 Mcps, the photopeak counts were 85% of the total incident counts, while the DLC had only 25% good counts. The low photopeak fraction in the DLC method was due to a high 75% count-loss due to pile-ups which placed the pile-up-event energy above the photopeak acceptance-window. The DLC method delayed the occurrence of pile-up due to its shorter pulse width, but at very high count rates, its fixed pulse-width still made it more vulnerable to pile-ups (FIG. 16) than the PPC method, which has a variable signal-integrating time and count-recovery capability. Hence, the photopeak counts collected by the PPC method is 3.3 times more than the DLC method at 2 Mcps. The pulse-shaping method only maintained 35% at 0.25 Mcps, and there was no useful photopeak data above 0.25 Mcps because of pile-ups (FIG. 15).

The importance of an effective remnant light subtraction for every triggering event is demonstrated in FIGS. 17A–F, especially at very high counting rates. At 600 Kcps, a simple weighted-sum method (SWS) without remnant subtraction yielded an acceptable but worse spectrum compared to the present invention. However, at high counting rates 1–3.5 Mcps, the energy measurement errors of SWS are significant. Above 2 Mcps for NaI(T1), most events are riding on the signal of other events (see Table 2 and FIG. 16), and SWS would measure large energy errors on most events and cause severe count-loss outside the photopeak acceptance window. The SWS energy measurement errors demonstrated here (shaded spectra in FIGS. 17A–F) should be similar to that shown in U.S. Pat. No. 5,430,406 discussed above. FIGS. 15–17 demonstrates the count and energy recovery/restoration capabilities of the present invention.

C. Example III

As shown in FIGS. 18A–C, a Monte Carlo simulation of the torso (with liver, kidneys, and bladder) was performed to demonstrate the effect of pile-ups in imaging at 2 Mcps for: (a) the method of the present invention (FIG. 18A); (b) the pulse-clipping method (256 ns) (FIG. 18B); and (c) the regular fixed integration method (1 μs) (FIG. 18C). The study simulates the electronic processing of each method in a gamma camera. The results are shown in FIGS. 18A–C. At 2 Mcps, the present invention method showed all the uptake organs; the conventional method shows no organs; the pulse-clipping result was in between the two, with high pile-up artifacts between the two kidneys and diminishing activities in the bladder and kidneys.

Besides preventing measurement errors from pile-ups, the present invention allows data acquisition time to be shortened significantly. This fast data acquisition is important in commercial/medical applications, as data acquisition time can be significantly reduced. As discussed above, the count loss with the conventional method is very high above 160,000 cps and saturates at 200,000 cps. Although the data appears to indicate that the conventional method can approach 200,000 cps, the pile-up fraction at this limit is very large, and the photopeak is badly distorted. Therefore, a large percentage of the data is not useful. The present invention can count over 2,000,000 cps with very little count loss, while preserving a very good photopeak, and all of the data is useful. Thus, the present invention is a significant improvement over the prior art.

Data from an embodiment of the present invention demonstrate that the invention significantly improves measurement of the energy of gamma rays at very high count-rates, even when multiple pile-up approaches 60% and single pile-up approaches 17% (nonpile-up at only 13%) at 2,000,000 cps. The data indicate that a 10–20 fold improvement in count-rate capability is feasible with the present invention.

These studies discussed above showed that the methods of the present invention are feasible. Compared to the pulse-shaping method, it has a 15 times higher counting rates, and yet at low counting rates, the PPC energy resolution is the same as the standard pulse-shaping method. The PPC energy resolution only degraded slowly from 10.9% at 50 Kcps to 15% at 2000 Kcps. Compared to the pulse-clipping technique, the PPC method has better energy resolution at regular count rates (10.9% vs 15%) and 3.3 times higher photopeak (non-pile-up) counts at 2000 Kcps. The count and energy recovery capability of the present invention at very high count rates is important for extending the maximum count rates of scintillation detectors.

All of the methods and apparatus disclosed and claimed herein can be made and executed without undue experimentation in light of the present disclosure. While the compositions and methods of this invention have been described in terms of preferred embodiments, it will be apparent to those of skill in the art that variations may be applied to the methods and apparatus and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

APPENDIX (1) Energy Pile-up Prevention Formulae Algebra

Suppose at time $t_j$, a j-th gamma ray ($\gamma_j$) is detected. The j-th gamma ray is a pile-up event on top of two preceding gamma rays $\gamma_{j-1}$ and $\gamma_{j-2}$. From Knoll, 4979, the instantaneous scintillation emission of a scintillator after detecting a gamma ray is $$\xi(t) = \frac{E}{\tau} e^{-(t-t_j)/\tau} \qquad (1)$$

where E is the total scintillation signal generated by the scintillator, and E is proportional to the energy of the gamma ray detected. The instantaneous signal at time $t_j$ for $t_j < t < t_{j+1}$, contains emission from three gamma rays $\gamma_{j-2}, \gamma_{j-1}, \gamma_j$, and is given by, $$q(t) = \frac{E_j}{\tau} e^{-(t-t_j)/\tau} + \frac{E_{j-1}}{\tau} e^{-(t-t_{j-1})/\tau} + \frac{E_{j-2}}{\tau} e^{-(t-t_{j-2})/\tau} \qquad (2)$$

$$= \frac{E_j}{\tau} e^{-(t-t_j)/\tau} + \left[\frac{E_{j-1}}{\tau} e^{-(t-t_{j-1})/\tau}\right] e^{-(t-t_{j-1})/\tau} +$$

$$\left[\frac{E_{j-2}}{\tau} e^{-(t-t_{j-2})/\tau}\right] e^{-(t-t_j)/\tau}$$

$$= [E_j + E_{j-1} e^{-(t_j-t_{j-1})/\tau} + \qquad (3)$$

$$E_{j-2} e^{-(t_j-t_{j-2})/\tau}] \left[\frac{1}{\tau} e^{-(t-t_{j-1})/\tau}\right]$$

If q(t) is amplified or weighted by an amplification factor τ:

$$\tau q(t) = [E_j + E_{j-1} e^{-(t_j-t_{j-1})/\tau} + E_{j-2} e^{-(t_j-t_{j-2})/\tau}][e^{-(t-t_j)/\tau}] \qquad (4)$$

If q(t) is only integrated from $t_j$ to t (this implicitly means that the integrator was discharged or zeroed just before $t_j$) from equation (3), $$\int_{t_j}^{t} q(u)du = [E_j + E_{j-1} e^{-(t_j-t_{j-1})/\tau} + E_{j-2} e^{-(t_j-t_{j-2})/\tau}][1 - e^{-(t-t_j)/\tau}] \qquad (5)$$

If equation (4) and (5) are summed, the weighted sum within the time period of gamma-ray $\gamma_j$ will be:

$$S_j = \tau q(t) + \int_{t_j}^{t} q(u)du = E_j + [E_{j-1} + E_{j-2} e^{-(t_{j-1}-t_{j-2})/\tau}] e^{-(t_j-t_{j-1})/\tau} \qquad (6)$$

The same analysis is now applied to the preceding time period where $t_{j-1} < t < t_j$ (the time period of $\gamma_{j-1}$). From equation (1) and FIG. 13, the instantaneous signal after the onset of $\gamma_{j-1}$ is:

$$q(t) \frac{E_{j-1}}{\tau} e^{-(t-t_{j-1})/\tau} + \frac{E_{j-2}}{\tau} e^{-(t-t_{j-2})/\tau} \qquad (7)$$

The weighted sum for this period is:

$$S_{j-1} = \tau q(t) + \int_{t_{j-1}}^{t} q(u)du \qquad (8)$$

Hence $S_{j-1}$ is the term inside the square bracket of equation (6), and equation (6) becomes:

$$S_j = E_j + S_{j-1} e^{-(t_j-t_{j-1})/\tau} \quad \text{or} \quad E_j = S_j - S_{j-1} e^{-(t_j-t_{j-1})/\tau} \qquad (9)$$

Hence the energy deposition of the j-th gamma ray can be derived from the j-th weighted sum minus the preceding weighted sum decreased by a emission decay factor, provided that the integrator is discharged immediately before the arrival of the j-th gamma. Note that the weighted-sum Sj as shown in equation (6) is not a measurement of energy of the j-th event, it is the measurement of the total energy trapped inside the scintillator just after the j-th event hit; i.e., $S_j$ includes the energy of the j-th event and all the remnant energy of previous multiple-pile-ups when the j-th event is deposited.

Equation (9) is an exact solution, regardless of how many previous gamma tails on which the j-th gamma is riding. The present invention thus provides the first method that attempts to recover all triggering events and compensating for multiple-pile-up exactly. Thus, the present invention may achieve higher count rates than possible with known methods.

Equation (9) can be easily understood intuitively. If there is no pile-up, $S_j$ is the detected energy of the j-th gamma ray (independent to when $S_j$ is sampled). If there are pile-ups, $S_j$ is the total energy in the detector in the j-th period (independent to when $S_j$ is sampled), which includes the detected energy of the j-th gamma ray and the remnant emission of all the preceding gamma ray. This j-th remnant emission is simply the total energy in the preceding period $(S_{j-1})$ decreased by the emission decay factor governed by the time difference between the j-th gamma and its preceding gamma.

(2) Pile-up Prevention Formulae for Gamma-Camera Anger-Positioning

In Anger-position method, assuming that no pile-up occurs, the γ-location is estimated by the centroid calculation:

$$X = \frac{\sum_i X_i E_i}{\sum_i E_i} = \frac{X'}{Z}; \quad Z \equiv \sum_i E_i \tag{10}$$

where $E_i$ is the total signal received by Photomultiplier-i (PMT-i) when a γ-ray is detected, and $X_i$ is the physical location of PMT-i. X' is the prenormalized pseudo-position signal which needs to be normalized by the total detected energy Z of the γ-ray, to generate the centroid location X. X' can be defined as:

$$X' = X_+ - X_-$$

If at time $t_1$, the first γ-ray with energy $Z_1$ is detected, the total energy (after signal integration) distributed to PMT-1, PMT-2, ..., PMT-n are $E_{11}, E_{12}, \ldots, E_{1n}$, respectively. The total integrated energy detected by the camera is:

$$Z_1 = \Sigma_i E_{1i} \tag{11}$$

From equation (10), the prenormalized position X' for conventional Anger positioning is:

$$X_1' = \Sigma_i X_i E_{1i} \tag{12}$$

In conventional Anger-position, $E_{1i}$ in equation (12) are the integrated PMT signals (integrated for 0.6–1 μs), and therefore $X_1'$ in equation (12) is a static quantity obtained after a fixed 1 μs integration time. Hence, if there is a pile-up during the integration time, $X_1'$ will be wrong. In the method of the present invention, the instantaneous prenormalized position X'(t) is used:

$$X_1'(t) = \sum_i X_i \frac{E_{1i}}{\tau} e^{-(t-t_1)/\tau}$$

The weighted instantaneous prenormalized position is:

$$\tau X_1'(t) = \Sigma_i X_i E_{1i} e^{-(t-t_1)/\tau} \tag{13}$$

The integrated prenormalized position is:

$$\int_{t_1}^{t} X_1'(u) du = \Sigma_i X_i E_{1i}(1 - e^{-(t-t_1)/\tau}) \tag{14}$$

If equation (13) and (14) are summed, the weighted Sum of $X'^1(t)$ is given by:

$$SX_1' = \tau X_1'(t) + \int_{t_1}^{t} X_1'(u) du = \Sigma_i X_i E_{1i} \tag{15}$$

From equation (12) and equation (15), we obtain $SX_1' = X_1'$. Hence, if the event $\gamma_1$ is not a pile-up on previous events, the weighted sum, $SX_1'$, is also an estimation of the Anger centroid-location for the gamma ray ($\gamma_{1,i}$), just like static quantity $X_1'$ in equation (12) for conventional Anger-method. Furthermore, the weighted sum $SX_1'$ is a time independent quantity which can be sampled at anytime and still provide an unbiased estimation of the prenormalized location. Therefore sum position $SX_1'$ is just like its energy-counterpart weighted sum $S_i$ in equation (6).

However, if the event ($\gamma_1$) is a pile-up on a previous gamma-ray ($\gamma_0$), the prenormalized position weighted sum will not be equal to the true prenormalized position of $\gamma_1$, because $SX_1'$ contains the remnant prenormalized position weighted-sum $SX_0'$ generated by the remnant scintillation of $\gamma_0$. The $\gamma_0$ remnant position weighted-sum (a position vector) adds an error-position vector to the $\gamma_1$ position. The magnitude of this error vector increases if the time lapse $(t_1-t_0)$ between $\gamma_0$ and $\gamma_1$ decreases. These positioning errors are especially severe when the count rates are very high that (a) most of the events ride on the remnant of previous events and (b) multiple-event pile-ups are the norm. Hence, the general solution to derive the true prenormalized position of each event $\gamma_1$ requires the subtraction of the remnant-position signals of previous events from the prenormalized position weighted-sum, $SX_i'$ and $SY_i'$, triggered by each $\gamma_i$.

In the general case where any event can be riding on the signals of one or more previous events, the weighted instantaneous prenormalized position signal triggered by an incident event $\gamma_m$ is given by the superposition, $$\tau X_m'(t) = \Sigma_i X_i E_{m,i} e^{-(t-t_m)/\tau} + \Sigma_i X_i E_{m-1,i} e^{-(t-t_{m-1})/\tau} + \Sigma_i X_i E_{m-2,i} e^{-(t-t_{m-2})/\tau} + \ldots \tag{16}$$

where $t_m < t < t_{m+1}$. The corresponding integrated prenormalized position signal is given by:

$$\int_{t_m}^{t} X_m'(u) du = \tag{17}$$

$$\sum_i X_i E_{m,i}(1 - e^{-(t-t_m)/\tau}) + \sum_i X_i E_{m-1,i} e^{-(t_m-t_{m-1})/\tau}(1 - e^{-(t-t_m)/\tau}) +$$

$$\sum_i X_i E_{m-2,i} e^{-(t_m-t_{m-2})/\tau}(1 - e^{-(t-t_m)/\tau}) + \ldots$$

This integration can be carried out by first zeroing the integrator just before the onset of $\gamma_m$, and then restarting the integration immediately.

Summing equations (16) and (17), the weighted sum of the prenormalized position signal is:

$$SX_m' = \sum_i X_i E_{m,i} + \tag{18}$$

$$\sum_i X_i E_{m-1,i} e^{-(t_m-t_{m-1})/\tau} + \sum_i X_i E_{m-2,i} e^{-(t_m-t_{m-2})/\tau} + \ldots$$

-continued $$= \sum_i X_i E_{m,i} + \qquad (19)$$

$$e^{-(t_m-t_{m-1})/\tau}\left[\sum_i X_i E_{m-1,i} + \sum_i X_i E_{m-2,i} e^{-(t_{m-1}-t_{m-2})/\tau} + \ldots\right]$$

It can be observed that the term inside the bracket in equation (19) is simply $SX'_{m'-1}$ (see equation (18)). The recurring relationship reduced equations (19) and (12) to $$SX'_m = \sum_i X_i E_{m,i} + e^{-(t_m-t_{m-1})/\tau} SX'_{m-1}$$

$$= X'_m + e^{-(t_m-t_{m-1})/\tau} SX'_{m-1}$$

Therefore, the prenormalized Anger-logic position ($X'_m$, $Y'_m$) of $\gamma_m$ can be derived from the weighted prenormalized position sums of $\gamma_m$, $\gamma_{m-1}$, and the time-lapse between the two events, $$X'_m = SX'_m - SX'_{m-1} e^{-(t_m-t_{m-1})/\tau}$$

$$Y'_m = SY'_m - SY'_{m-1} e^{-(t_m-t_{m-1})/\tau} \qquad (20)$$

Since the derivation of equation (20) assumes that $\gamma_m$ is riding on any numbers of preceding events, equation (20) provides an exact determination of the position of $\gamma_m$, even when it is part of a multiple-event pile-up.

The pile-up-free prenormalized position ($X'_m$, $Y'_m$) will then be renormalized by the energy of $\gamma_m$ as in conventional Anger-logic to remove the energy-scaling effect in generating the position of $\gamma_m$. Hence, the energy of $\gamma_m$ also has to be extracted correctly from a multiple-event pile-up if the position of $\gamma_m$ is to be decoded accurately. The pile-up-free energy of $\gamma_m$ can also be derived from the energy weighted-sum of $\gamma_m$, $\gamma_{m-1}$, and the time lapse between these two events, $$E_m = S_m - S_{m-1} e^{-(t_m-t_{m-1})/\tau} \qquad (21)$$

where $S_m$ is the sum of the weighted instantaneous scintillation signal and the integral of the instantaneous scintillation signal.

REFERENCES

The following references, to the extent that they provide exemplary procedural or other details supplementary to those set forth herein, are specifically incorporated herein by reference.

Alavi, Karp, Freifelder, Smith, Rigin, Kilroy, Mozley, "Initial Clinical Experience with Ultra High Resolution, Large Field of View, Volume Imaging Head Penn-PET Scanner," *J. Nucl. Med.*, 5(37):277, 1996.

Clarke, Saw, Leong, Serafini, "SPECT Imaging of $^{131}$I (364 KeV): Importance of Collimation," *Nucl Med Commun*, 1(6):41–47, 1985.

Eary, Press, Badger, Durack, Richter, Addison, Krohn, Fisher, Porter, Williams, Martin, APPClbaum, Levy, Brown, Miller, Nelp, Bernstein, "Imaging and Treatment of B-Cell Lymphoma," *J. Nucl. Med.*, 8(31):1257–1268, 1990.

Eary, Pollard, Durack, Bice, Lewellen, Mathews, Press, Nelp, APPClbaum, Berstein, "Post Therapy Imaging in High Dose I-131 Radioimmunotherapy Patients," *Med Phys*, 7(21):1157–1162, 1994.

Freifelder, Karp, Geagan, Muehllehner, "Design and performance of the Head Penn-PET scanner," *IEEE Transactions on Nuclear Science*, 41(4):1436–1440, August 1994.

Glass, Nelleman, Hines, Mandelkern, Blahd, "Initial Coincidence Imaging Experience with a SPECT/PET Dual Head Camera," *J. Nucl. Med.*, 5(37):53, 1996.

Jaszczak, "Physical characteristics of SPECT systems, September, 1982," *J Comput Assist Tomogr.*, 6:1205–1215, 1982.

Karp and Muehllehner, "Performance of a position-sensitive scintillation detector," *Phys. Med. Biol.*, 30:643–655, 1986.

Karp, Muehllehner, Beerbohm, Mankoff, "Event localization in a continuous scintillation detector using digital processing," *IEEE Transactions on Nuclear Science*, 33(1):550–555, 1986.

Knoll, *Radiation detection and measurement*, Wiley Press, 1979.

Lewellen, Bice, Pollard, Zhu, Plunkett, "Evaluation of a clinical scintillation camera with pulse tail extrapolation electronics," *J. Nucl. Med.*, 30:1554–1558, 1989.

Lewellen, Miyaoka, Kaplan, Kohlmyer, Costa, Jansen, "Preliminary Investigation of Coincidence Imaging with a Standard Dual-Headed SPECT System," *J. Nucl. Med.*, 5(36):175, 1995.

Li, Ph.D. Dissertation, University of Science and Technology of China, Hefei, China, August 1996.

Miyaoka, Costa, Lewellen, Kaplan, Kohlmyer, Jansen, "Coincidence Mode Imaging Using A Standard Dual-Headed Gamma Camera," *J. Nucl. Med.*, 5(37):223, 1996a.

Miyaoka, Costa, Lewellen, Kohmyer, Kaplan, Jansen, Stearn, "Coincidence imaging using a standard dual head gamma camera," *IEEE Nuclear Science Symposium and Medical Imaging Conference, Conference Record* October, 1996b.

Muehllenhner and Karp, "A positron camera using position sensitive detectors: PENN-PET," *J. Nucl Med.*, 27:90–98, 1986.

Muehllehner, Geagan, Countryman, Nellemann, "SPECT Scanner with PET Coincidence Capability," *J. Nucl. Med.*, 5(36):70, 1995.

Nicholson, *Nuclear Electronics*, Wiley Press, 1974.

Pollard, Bice, Eary, Durack, Lewellen, "A Method for Imaging Therapeutic Doses of Iodine-131 with a Clinical Gamma Camera," *J. Nucl. Med.*, 33(5):771–776, 1992.

Sorenson and Phelps, *Physics in Nuclear Medicine*, Saunders Press, 1987.

Tanaka, Nohara, Murayama, "Variable sampling time technique for improving count rate performance of scintillation detectors," *Nucl Instr Meth*, 158:459–466, 1979.

What is claimed is:

1. An apparatus for dynamically detecting energy of each one of a plurality of incoming signals received from a detector, without pile-up of previous ones of said plurality of incoming signals, comprising:

a delay circuit connected to receive an incoming signal from said detector, said delay circuit passing said incoming signal from an input to an output of said delay circuit after a time delay;

a trigger circuit connected to receive said incoming signal from said detector, said trigger circuit generating a triggering signal upon receipt of a subsequent one of said plurality of incoming signals at said trigger circuit;

a computation circuit connected to said output of said delay circuit, said computation circuit determining a weighted value of said incoming signal;

a sampling circuit connected to receive said weighted value from said computation circuit, said sampling circuit passing said weighted value from an input to an output of said sampling circuit upon receipt of said triggering signal; and a residual subtraction circuit connected to said output of said sampling circuit, said residual subtraction circuit subtracting a residual signal value corresponding to a residual weighted value of said previous ones of said plurality of incoming signals, said residual subtraction circuit providing an output signal corresponding to said energy of said incoming signal.

2. The apparatus of claim 1, said computation circuit comprising an amplifier connected to an integrator connected to an adder.

3. The apparatus of claim 1, said computation circuit comprising an amplifier connected to a switch connected to two integrators connected to a switch connected to an adder.

4. The apparatus of claim 1, said computation circuit comprising a plurality of channels each including an integrator connected to an adder connected to a said sampling circuit, each of said channels adapted to switchably accept said plurality of incoming signals.

5. The apparatus of claim 1, said weighted value comprising a combination of an integrated value of said incoming signal and an instantaneous value of said incoming signal.

6. The apparatus of claim 1, further comprising a smoothing circuit connected between said detector and said delay circuit.

7. The apparatus of claim 6, said smoothing circuit comprising a low-pass filter.

8. The apparatus of claim 1, further comprising a discharge circuit connected to said calculation circuit, said discharge circuit discharging said calculation circuit upon receipt of said triggering signal.

9. The apparatus of claim 1, said trigger circuit comprising a discriminator and Schmitt trigger.

10. The apparatus of claim 1, wherein said residual subtraction circuit comprises a look-up table.

11. The apparatus of claim 1, said detector comprising a scintillator.

12. The apparatus of claim 1, further comprising a digital signal processor connected to said residual subtraction circuit.

13. The apparatus of claim 1, further comprising an A/D converter connected between said sampling circuit and said residual subtraction circuit.

14. The apparatus of claim 1, said delay circuit, said computation circuit, and said sampling circuit together comprising a pile-up prevention circuit.

15. The apparatus of claim 14, further comprising a plurality of pile-up prevention circuits.

* * * * *

UNITED STATES PATENT AND TRADEMARK OFFICE
CERTIFICATE OF CORRECTION

PATENT NO. : 6,525,322 B2 Page 1 of 1
APPLICATION NO. : 09/957122
DATED : February 25, 2003
INVENTOR(S) : Wong et al.

It is certified that error appears in the above-identified patent and that said Letters Patent is hereby corrected as shown below:

Column 1, lines 6-12, delete the entire paragraph and insert the following paragraph therefor:

--This invention was made with government support under NIH-RO1-CA61880, NIH-RO1-CA58980; NIH-RO1-CA76246, and NIH-RO1-CA58980S1 awarded by the National Institutes of Health - National Cancer Institute. The Government has certain rights in the invention. This invention claims the benefit of U.S. Provisional Application Ser. No. 60/045,836, by Wai-Hoi Wong, et al., filed May 7, 1997.--

Signed and Sealed this

Sixth Day of November, 2007

JON W. DUDAS
*Director of the United States Patent and Trademark Office*